(12) United States Patent
Fridman

(10) Patent No.: US 8,324,194 B2
(45) Date of Patent: Dec. 4, 2012

(54) COMBINATION THERAPY FOR THE TREATMENT OF CANCER

(75) Inventor: Jordan S. Fridman, Newark, DE (US)

(73) Assignee: Incyte Corporation, Wilmington, DE (US)

( * ) Notice: Subject to any disclaimer, the term of this patent is extended or adjusted under 35 U.S.C. 154(b) by 468 days.

(21) Appl. No.: 11/602,659

(22) Filed: Nov. 21, 2006

(65) Prior Publication Data

US 2007/0117809 A1    May 24, 2007

Related U.S. Application Data

(60) Provisional application No. 60/738,919, filed on Nov. 22, 2005.

(51) Int. Cl.
*A01N 43/00* (2006.01)
*A61K 31/33* (2006.01)
*A61K 31/497* (2006.01)

(52) U.S. Cl. ............... 514/183; 514/253.04; 514/254.08

(58) Field of Classification Search .................. 514/183, 514/253.04, 254.08
See application file for complete search history.

(56) References Cited

U.S. PATENT DOCUMENTS

| 2003/0158166 | A1* | 8/2003 | Thurlimann .................. 514/182 |
| 2004/0024044 | A1* | 2/2004 | Di Salle et al. ............... 514/414 |
| 2004/0247602 | A1  | 12/2004 | Friedman et al. |
| 2004/0259896 | A1* | 12/2004 | Yao et al. ....................... 514/278 |
| 2005/0113344 | A1  | 5/2005 | Li et al. |
| 2005/0250789 | A1  | 11/2005 | Burns et al. |

FOREIGN PATENT DOCUMENTS

| WO | WO 02/072106 | 9/2002 |
| WO | WO 2004/096139 | 11/2004 |
| WO | WO 2007/143600 | 12/2007 |

OTHER PUBLICATIONS

Robertson (Clinical Therapeutics (2002) 24 Suppl. A A17-A30).*
Benz et al., "Estrogen-Dependent, Tamoxifen-Resistant Tumorigenic Growth of MCF-7Cells Transfected with HER2/*neu*," Breast Cancer Research and Treatment 24: 85-95 (1992).
Blobel et al., "Adams: Key Components in EGFR Signalling and Development," *Nature* 6: 32-43 (2005).
Carney et al., "Potential Clinical Utility of Serum HER-2/*neu* Oncoprotein Concentrations in Patients with Breast Cancer," *Clinical Chemistry*, 49(10): 1579-1598 (2003).
Chang, C and Werb, Z., "The Many Faces of Metalloproteases: Cell Growth, Invasion, Angiogenesis and Metastasis," Trends in Cell Biology 11(11): S37-S43 (2001).
Dowsett et al., "HER-2 Amplification Impedes the Antiproliferative Effects of Hormone Therapy in Estrogen Receptor-Positive Primary Breast Cancer," *Cancer Research*, 61: 8452-8458 (2001).
Hynes, N. and Lane, H., "ERBB Receptors and Cancer: The Complexity of Targeted Inhibitors," *Nature Reviews*, 5:341-354 (2005).

Kurokawa H. and Arteaga C., "ErgB (HER) Receptors Can Abrogate Antiestrogen Action in Human Breast Cancer by Multiple Signaling Mechanisms," Clinical Cancer Research, 9:511s-515s (2003).
Kurokawa H. and Arteaga C., "Inhibition of erbB Receptor (HER) Tyrosine Kinases as a Strategy to Abrogate Antiestrogen Resistance in Human Breast Cancer," *Clinical Cancer Research* 7: 4436s-4442s (Suppl.) (2001).
Kurokawa et al., "Inhibition of HER2/*neu* (*erb*B-2) and Mitogen-Activated Protein Kinase Enhances Tamoxifen Action Against HER2-Overexpressing, Tamoxifen-Resistant Breast Cancer Cells," Cancer Research, 60: 5887-5894 (2000).
Lipton et al., "Serum HER-2/neu and Response to the Aromatase Inhibitor Letrozole Versus Tamoxifen," *Journal of Clinical Oncology*, 21(10), 1967-1972 (2003).
Liu et al., "Inhibition of HER-2/*neu* Kinase Impairs Androgen receptor Recruitment to the Androgen Responsive Enhancer," *Cancer Res.*, 65(8); 3404-3409 (2005).
Massarweh et al., "Mechanisms of Tumor Regression and Resistance to Estrogen Deprivation and Fulvestrant in a Model of Estrogen Receptor-Positive, HER-2/*neu*-Positive Breast Cancer," *Cancer Res.*, 66(16): 8266-8273 (2006).
Mellinghoff et al., "HER2.neu Kinase-Dependent Modulation of Androgen Receptor Function Through Effects on DNA Binding and Stability," *Cancer Cell* 6: 517-527 (2004).
Miller et al., "Emergence of MCF-7 Cells Overexpressing a Transfected Epidermal Growth Factor Receptor (EGFR) Under Estrogen-Depleted Conditions: Evidence for a Role of EGFR in Breast Cancer Growth and Progression" *Cell Growth & Differentiation* 5:1263-1274 (1994).
Moss M. and Lambert, M., "Shedding of Membrance Proteins by ADAm Family Proteases," *Essays in Biochemistry*, The Biochemical Society, London; pp. 141-153 (2002).
Newby et al., "Expression of Epidermal Growth Factor Receptor and c-erbB2 During the Development of Tamoxifen Resistance in Human Breast Cancer," *Clinical Cancer Research*, 3:1643-1651 (1997).
Osborne et al., "Upregulation of Estradiol C16α-hydorxylation in Human Breast Tissue: A Potential Biomarker of Breast Cancer Risk," *Journal of the National Cancer Institute* 85(23): 1917-1920.
Sabnis et al., "The Role of Growth Factor Receptor in Human Breast Cancer Cells Adapted to Long-Term Estrogen Deprivation" *Cancer Res.* 65(9): 3903-3910 (2005).
Schiff R. and Osborne C.K., "New Insight Into Estrogen Receptor-α-Function and Its Implication for Endocrine Therapy Resistance in Breast Cancer," *Breast Cancer Research* 7: 205-211 (2005).
Seals D. and Courtneidge S., "The ADAMs Family of Metalloproteases: Multidomain Proteins with Multiple Functions," *Genes & Development* 17:7-30 (2003).
Stabile et al., "Combined Targeting of the Estrogen Receptor and the Epidermal Growth Factor Receptor in Non-Small Cell Lung Cancer Shows Enhanced Anitproliferative Effects," *Cancer Res.*, 65(4): 1459-1651 (2005).

(Continued)

*Primary Examiner* — Marcos Sznaidman
(74) *Attorney, Agent, or Firm* — Fish & Richardson P.C.

(57) ABSTRACT

The present invention provides methods of treating cancer comprising treating a patient in need thereof with hormone therapy and administering to the patient a therapeutically effective amount of at least one metalloprotease inhibitor. The present invention also provides pharmaceutical compositions comprising a therapeutically effective amount of at least one hormone therapy agent, at least one metalloprotease inhibitor, and a pharmaceutically acceptable carrier.

3 Claims, 2 Drawing Sheets

OTHER PUBLICATIONS

Van Agthoven et al., "Ectopic Expression of Epidermal Growth Factor Receptors Induces Hormone Independence in ZR=75-1 Human Breast Cancer Cells," Cancer Research 52:5082-5088 (1992.).

Wright et al., "Expression of c-*erbB*-2 Oncoprotein: A prognostic Indicator in Human Breast Cancer," *Cancer Research*, 49: 2087-2090 (1989).

Gitler et al., "Preclinical models for defining efficacy of drug combinations: mapping the road to the clinic," Molecular Cancer Therapeutics 2:929-932 (2003).

Jelovac, et al, "Activation of Mitogen-Activated Protein Kinase in Xenografts and Cells during Prolonged Treatment with Aromatase Inhibitor Letrozole", *Cancer Research*, 65(12), 5380-5389, Jun. 15, 2005.

Abidi, S.M. Abbas et al., "Differential Influence of Antiestrogens on the in vitro Release of Gelatinases (type IV Collagenases) by Invasive and Non-invasive breast cancer cells", *Clinical and Experimental Metastasis*, vol. 15, No. 4, pp. 432-439, 1997; XP002487339.

Brown, P.D., "Ongoing Trials with Matrix Metalloproteinase Inhibitors", *Expert Opinion on Investigational Drugs*, vol. 9, No. 9, pp. 2167-2177, 2000; XP001008392.

Marson, L.P. et al., "Angiogenesis and Breast Cancer", *The Breast,*, vol. 7, No. 6, pp. 299-307, 1998; XP008094010.

Rau, K.M. et al., "The Mechanisms and Managements of Hormone-Therapy Resistance in Breast and Prostate Cancers", *Endocrine-Related Cancer*, vol. 12. No. 3, pp. 511-532, 2005; XP008094039.

Razandi, M. et al., Proximal Events in Signaling by Plasma Membrane Estrogen Receptors, *The Journal of Biological Chemistry*, vol. 278, No. 4, pp. 2701-2712, 2003; XP008094012.

Scatena, R., "Prinomastat, A Hydroxamate-Based Matrix Metalloproteinase Inhibitor. A Novel Pharmacological Approach for Tissue Remodelling-Related Diseases", *Expert Opinion on Investigational Drugs*, vol. 9, No. 9, pp. 2159-2165, 2000; XP001008391.

Zheng, C.J. et al., "Trends in Exploration of Therapeutic Targets", *Drug News and Perspectives,*, vol. 18, No. 2, pp. 109-127, 2005; XP008063814.

The International Search Report and Written Opinion for PCT/US2006/045151, dated Jul. 23, 2008.

International Examination Report for PCT/US2006/045151 dated Sep. 4, 2008.

Weinberg, et al., "New approaches to reverse resistance to hormonal therapy in human breast cancer", Drug Resistance Updates, vol. 8, pp. 219-233 (2005).

Yoneya, T. et at. "Identification of a novel, orally bioavailable estrogen receptor downregulator", Anti-cancer Drugs, vol. 16, No. 7, Aug. 2005, pp. 751-756.

* cited by examiner

COMBINATION THERAPY FOR THE TREATMENT OF CANCER

CROSS REFERENCE TO RELATED APPLICATION

This application claims the benefit of U.S. Ser. No. 60/738,919, filed Nov. 22, 2005, the disclosure of which is incorporated herein by reference in its entirety.

FIELD OF THE INVENTION

The present invention is directed to methods of treating cancer utilizing the synergistic effects of combinations of hormone therapy and metalloprotease inhibitors. The present invention is also directed to pharmaceutical compositions which contain at least one hormone therapy agent, at least one metalloprotease inhibitor, and a pharmaceutically acceptable carrier.

BACKGROUND OF THE INVENTION

The growth and survival of some types of cancer cells are known to be influenced by hormones which activate hormone receptors on/in target cells. For example, breast cancer cells have been shown to be highly dependent upon estrogen for proliferation and/or survival. Estrogen is thought to impact cell growth by binding to and activating the estrogen receptor (ER), a member of a large family of transcriptional regulators (reference herein to the "estrogen receptor" is meant to refer to all estrogen receptors). After binding of the estrogen ligand, the estrogen receptor is activated through phosphorylation and receptor dimerization. Activated ER regulates the transcription of a number of genes important to controlling cellular fate through its ability to bind estrogen response elements in the promoters of target genes and impact gene transcription (see, e.g., Osborne, et. al., J. Natl. Cancer Inst. 85, 1917-20 (1993), incorporated herein by reference in its entirety). The resulting changes in the transcriptional profile can impact, potentially, both the cell with the activated ER as well as neighboring cells.

The development of prostate cancer is also highly dependent on the activation of hormone receptors by androgens, e.g., dihydroxytestosterone. (Schiff & Osborne, Breast Cancer Res. 7, 205-211 (2005), incorporated herein by reference in its entirety). The prostate produces dihydroxytestosterone from testosterone through the action of 5-alpha-reductase. In the cytosol, dihydroxytestosterone binds to and activates the androgen receptor (reference herein to the "androgen receptor" is meant to refer to all androgen receptors). As in the case of the activated estrogen receptor, the activated androgen receptor can bind androgen response elements, thereby influencing gene expression and triggering cell proliferation.

Because of the dependence of tumor cell growth and survival on activated hormone receptors, hormone therapy treatments, also known as endocrine therapy treatments, have been developed that target these receptors in various ways. Both breast and prostate cancer frequently express these receptors and, thus, are susceptible to targeting of either the hormone receptors or the production of the hormone responsible for binding and activating the receptors (for example, estrogens and androgens) (Schiff & Osborne, Breast Cancer Res. 7, 205-211 (2005); Hynes & Lane, Natl. Rev. Cancer, 5, 341-45 (2005), each of which is incorporated herein by reference in their entireties). Such hormone therapies usually target either the receptors directly or lower the production of hormones which bind to and activate these receptors, thereby reducing mitogenic and/or survival signaling from the receptors.

While hormone therapy can be initially useful in reducing tumor growth or shrinking tumors, many patients do not respond to such therapy and those that do respond eventually become resistant to treatment. Such resistance often results despite the availability of different classes of hormone therapy treatments, and cross-resistance is not uncommon.

Resistance to hormone therapy is consistent with intrinsic or acquired activation of alternative signaling pathways sufficient to support tumor cell survival. Significant evidence implicates the ErbB pathway as playing some role in resistance to hormone therapy.

The ErbB receptors (also known as the EGF family of receptors) are a subclass of the receptor tyrosine kinase (RTK) family and include four members: 1) HER-1, also known as the epidermal growth factor receptor (EGFR); 2) HER-2, also known as erbB2, c-neu, or p185; 3) HER-3, also known as erbB3; and 4) HER-4, also known as erbB4. The biological consequence of ErbB receptor signaling is frequently associated with cellular differentiation, growth or survival. EGFR, HER-2, and HER-3 have been implicated in reduced clinical responsiveness to hormone therapy.

For instance, evidence supports the idea that EGFR activation may be sufficient, or at least contribute to estrogen independence and/or resistance to hormone therapy in breast cancer. For example, selection for resistance to the aromatase inhibitor, letrozole, in an estrogen dependent cell line resulted in concomitant activation of the EGFR pathway and sensitization to EGFR kinase inhibition (Sabnis, et. al., Cancer Res. 65, 3903-10 (2005), incorporated herein by reference in its entirety). Additionally, enforced expression of EGFR in multiple tamoxifen sensitive breast cancer cell lines resulted in estrogen independence and/or resistance to hormone therapy (Van Agthoven, et. al., Cancer Res. 52, 5082-88 (1992); Miller, et. al., Cell Growth Differ. 5, 1263-74 (1994), each of which are incorporated herein by reference in their entireties). Conversely, inhibition of EGFR signaling can restore responsiveness to hormone therapy (Kurokawa & Arteaga, Clin. Cancer Res. 7, 4436s-42s, 4411s-4412s (2001), incorporated herein by reference in its entirety).

Signaling from EGFR may also play a role in reducing the efficacy of hormone therapy for the treatment of non-small cell lung cancer (NSCLC) patients. For example, inhibition of the EGFR tyrosine kinase increased the anti-tumor activity when used in combination with the hormone therapy agent, fluvestrant, an estrogen receptor downregulator (Stabile, et. al. Cancer Res. 65, 1459-70 (2005), incorporated herein by reference in its entirety). This suggests that signaling from activated EGFR may decrease the effectiveness of hormone therapy treatments in NSCLC as well.

HER-2 has also been implicated in resistance to hormone therapy for breast cancer patients. For example, activation of HER-2 has been correlated with reduced clinical responsiveness to hormone therapy (Kurokawa & Arteaga, Clin. Cancer Res. 7, 4436s-42s, 4411s-4412s (2001); Wright, et. al. Cancer Res. 49, 2087-90 (1989), each of which is incorporated herein by reference in their entireties). Indeed, HER-2 expression is sufficient to convey anti-estrogen resistance (Benz, et. al., Breast Cancer Res. Treat. 24, 85-95 (1993), incorporated herein by reference in its entirety).

HER-2, as well as HER-3, also appears to be involved in the onset of hormone resistance in prostate cancer patients. Approximately, one-third of prostate cancer patients receive hormone therapy treatment aimed at disrupting the action of testicular and adrenal androgens. As with breast cancer, resistance is inevitable. Recent data suggests that signals emanating from HER-2 and HER-3 induce a "hormone-refractory" state (Mellinghoff, et. al., Cancer Cell 6, 517-27 (2004), incorporated herein by reference in its entirety).

In summary, substantial evidence suggests that signaling from ErbB receptors plays some role in reducing the clinical responsiveness to hormone therapy in several different types of cancer, as well as contributing to the development of resistance to hormone therapy. Accordingly, one approach to increasing clinical responsiveness to hormone therapy and limiting the development of resistance in patients is to reduce the mitogenic and survival signals from the ErbB family of receptors. Signaling from the ErbB receptors is a complex process, but an important step is activation of the ErbB receptors.

Signaling by the ErbB family of receptors is thought to be initiated by ligand binding which triggers homo- or hetero-receptor dimerization, reciprocal tyrosine phosphorylation of the cytoplasmic tails, and activation of intracellular signal transduction pathways. The availability of signalling competent ErbB ligands which bind to and activate the ErbB receptors is mediated by various metalloproteases. For example, the ADAM (A Disintegrin And Metalloprotease) family of zinc-dependent metalloproteases has been demonstrated to catalyze cell surface ectodomain shedding of specific proteins (Moss and Lambert, Essays in Biochemistry 38:141-153 (2002); Chang and Werb, Trends in Cell Biology 11:537-543 (2001); Seals and Courtneidge, Genes and Development 17:7-30 (2003), each of which is incorporated herein by reference in their entireties). Specifically, the ADAM family has been shown to cleave ligands responsible for activating the ErbB receptors (Blobel, Nat. Rev. Mol. Cell. Biol. 6, 32-43 (2005), incorporated herein by reference in their entireties). For example, ADAM10 has been demonstrated to cleave proteins such as APP and Notch as well as other cell surface proteins. It is particularly important to note that ADAM 10 can cleave the extracellular domain of heparin-binding epidermal growth factor-like growth factor (HB-EGF). This cleavage process leads to the generation of a soluble fragment of HB-EGF that can bind to and activate EGFR (HER-1). Hence, one approach to decrease signaling from the ErbB receptors, such as EGFR, would be to inhibit the metalloproteases responsible for the cleavage of the ErbB ligands, such as the extracellular domain of HB-EGF.

Additionally, the ADAM10 and ADAM 15 metalloproteases have been shown to cleave the extracellular domain (ECD) of the HER-2 receptor to yield a truncated, membrane-associated receptor (sometimes referred to as a "stub" and also known as p95), and a soluble extracellular domain (also known as ECD, ECD105, or p105). This activity of ADAM10 and ADAM15 was shown in U.S. Patent Appl. No. 2004/0247602, which is incorporated herein by reference in its entirety. As with other EGF receptor family members, loss of the extracellular ligand binding domain renders the HER-2 intracellular membrane-associated domain a constitutively active tyrosine kinase. It has therefore been postulated that cleavage of the ECD of HER-2 creates a constitutively active receptor that can directly deliver growth and survival signals to the cancer cell. Furthermore, the truncated form of HER-2 receptor (p95) has been shown to interact with and activate signaling through EGFR (HER-1). Hence, another approach to decreasing signaling from both HER-2 and EGFR would be to inhibit formation of the truncated HER-2 receptor (p95).

Additionally, high levels of circulating HER-2 ECD in breast cancer patients has been correlated with reduced response rates to multiple hormone therapies and overall poor prognosis (Lipton, et. al., J. Clin. Oncol. 21, 1967-72 (2003); Carney, et. al. Clin. Chem. 49, 1579-98 (2003), each of which is incorporated herein by reference in their entireties). Hence, another approach to reducing the signaling from the ErbB receptors would be to reduce the formation of HER-2 ECD.

Nonresponsiveness and resistance to hormone therapy continue to present significant roadblocks to the successful treatment of cancer patients with hormone therapy. Accordingly there is an acute need to develop methods and compositions that increase the clinical responsiveness to hormone therapy and that inhibit or stop the development of resistance in patients. This invention addresses these needs and others.

SUMMARY OF THE INVENTION

The present invention provides methods of treating cancer comprising treating a patient in need thereof with hormone therapy and administering to the patient a therapeutically effective amount of at least one metalloprotease inhibitor (MPI).

The present invention further provides pharmaceutical compositions comprising at least one metalloprotease inhibitor (MPI), at least one hormone therapy agent, and a pharmaceutically acceptable carrier.

The present invention further provides methods of inhibiting growth of a tumor in a patient comprising treating a patient in need thereof with hormone therapy and administering to the patient a therapeutically effective amount of at least one metalloprotease inhibitor (MPI).

The present invention further provides methods of lowering a patient's resistance to hormone therapy comprising treating a patient in need thereof with hormone therapy and administering to the patient a therapeutically effective amount of at least one metalloprotease inhibitor (MPI).

The present invention further provides methods of inhibiting onset of a hormone-refractory state comprising treating a patient in need thereof with hormone therapy and administering to the patient a therapeutically effective amount of at least one metalloprotease inhibitor (MPI).

The present invention further provides methods of inhibiting tumor cell proliferation in a patient comprising treating the patient in need thereof with hormone therapy and administering to the patient a therapeutically effective amount of at least one metalloprotease inhibitor (MPI).

The present invention further provides methods of inhibiting metastasis of cancer comprising treating a patient in need thereof with hormone therapy and administering to the patient a therapeutically effective amount of at least one metalloprotease inhibitor (MPI).

The present invention further provides methods of inducing quiescence in tumor cell growth after the cessation of treatment comprising treating a patient in need thereof with hormone therapy and administering to the patient a therapeutically effective amount of at least one metalloprotease inhibitor (MPI) for a period of time, followed by ceasing of treatment.

DETAILED DESCRIPTION

Figure 1:
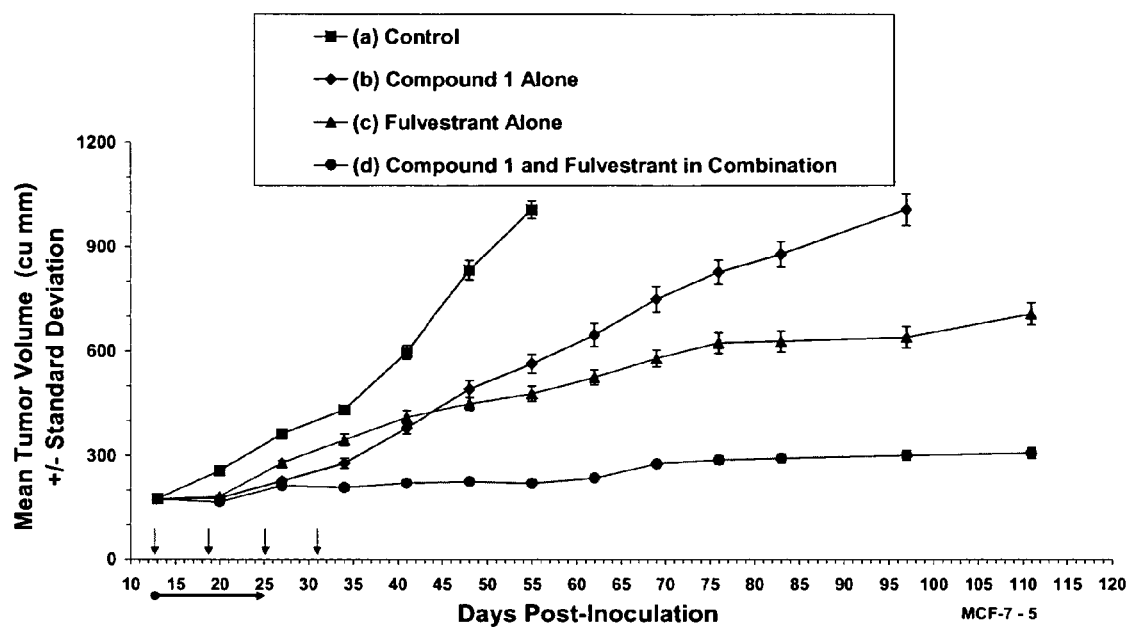
FIG. 1: Graph of mean tumor volume (cubic mm) for mice bearing subcutaneous MCF-7 human breast cancer xenografts plotted as a function of the number of days post-inoculation of the tumors into the mice. These breast cancer cells do not have an amplified HER-2 mutation, but grow in an estrogen dependent manner.

In one aspect, the present invention provides a method of treating cancer comprising treating a patient with hormone therapy and administering to the patient a therapeutically effective amount of at least one metalloprotease inhibitor (MPI). In another aspect, the present invention relates to the discovery that a combination of hormone therapy with a metalloprotease inhibitor (MPI) provides a synergistic inhibitory effect on the growth of cancer cells. Accordingly, the present invention provides a method of treating cancer comprising treating a patient with hormone therapy and administering to the patient at least one metalloprotease inhibitor (MPI), where the hormone therapy and MPI are provided in a synergistically effective amount. By "synergistically effective amount" is meant sufficient amounts and relative ratios such that there is synergism with respect to inhibiting growth and/or inhibiting the spread of cancer cells.

The definitions of terms provided herein refer to every reference to said terms throughout the present application and are not intended to be restricted to one particular embodiment of the invention.

As used herein, the term "MPI" refers to a metalloprotease inhibitor. As used herein, the term "metalloprotease inhibitor" refers any compound or substance that blocks, curbs or lessens the biological activity of a metalloprotease associated in any way with the ErbB family of receptors or their ligands. Such "biological activity" includes, but is not limited to cleavage of any ErbB ligand or HER-2. Such "biological activity" also includes, but is not limited to, cleavage of HER-2 such as the cleavage of HER-2 to form p95, ECD, or both. Because the cleavage of HER-2 to form p95 has been implicated as playing a role in the progression of cancer in HER-2 overexpressing cells, the biological activity of ADAM10 or ADAM15 as used herein also encompasses the potential to inhibit cell growth or induce cell death, and other anticarcinogenic effects.

As used herein, the term "ErbB receptor" refers to one of the members of the ErbB family of receptors, also referred to as the EGFR family of receptors. As used herein, the terms "ErbB family of receptors" and the "EGFR family of receptors" are interchangeable and refer to a group of receptor tyrosine kinases including 1) HER-1, also known as the epidermal growth factor receptor (EGFR); 2) HER-2, also known as erbB2, c-neu, or p185; 3) HER-3, also known as erbB3; and 4) HER-4, also known as erbB4. As used herein, a "ErbB ligand" refers to any ligand which can bind to a ErbB receptor. Such "ErbB ligand" also includes a ligand which binds to and activates any member of the ErbB family of receptors.

In some embodiments, the MPI is an ADAM inhibitor. In some embodiments, the MPI is an ADAM10, ADAM15, or ADAM17 inhibitor. In some embodiments, the MPI is an ADAM10 inhibitor.

As used herein, the term "ADAM" refers to the ADAM (A Disintegrin And Metalloprotease) family of proteases. As discussed previously, these metalloproteases has been demonstrated to catalyze cell surface ectodomain shedding of specific proteins (Moss and Lambert, Essays in Biochemistry 38:141-153 (2002); Chang and Werb, Trends in Cell Biology 11:537-543 (2001); Seals and Courtneidge, Genes and Development 17:7-30 (2003), incorporated herein by reference in their entireties). The domain structure of ADAM family members places the protease catalytic domain of these type I membrane proteins extracellularly. From the amino terminus of the protein, the domains include a pro domain, catalytic domain, disintegrin domain, cysteine rich region and EGF repeat followed by the transmembrane domain and cytoplasmic tail. The pro domain is processed to form the mature proteolytically active form. The disintegrin domain may be involved in adhesion or substrate recognition and binding. As previously discussed, this class of metalloproteases can cleave ligands that bind to and activate the ErbB class of receptors. This class of metalloproteases can also cleave HER-2.

As used herein, the term "ADAM inhibitor" refers to a MPI that inhibits the biological activity of the ADAM metalloprotease. Such "biological activity" includes, but is not limited to cleavage of any ErbB ligand or HER-2. Such "biological activity" also includes, but is not limited to, cleavage of HER-2, and more particularly, the cleavage of HER-2 to form p95, ECD, or both. Example ADAM inhibitors include, for example, inhibitors of ADAM10, ADAM15, and/or ADAM17.

In some embodiments, the MPI inhibits the cleavage of ErbB ligands. As previously, ErbB ligands can bind to and activate ErbB receptors. Accordingly, in some embodiments, the MPI inhibits ErbB receptor signaling by inhibiting cleavage of ErbB ligands.

In some embodiments, the MPI inhibits cleavage of HER-2. In some embodiments, the MPI inhibits the release of an extracellular domain (ECD) portion of a HER-2 on a HER-2 expressing cell. In some embodiments, the MPI inhibits formation of p95 on a HER-2 expressing cell.

As used herein, the term "cleavage of HER-2" refers to the process whereby the full-length HER-2 polypeptide (p185) is cleaved to produce a p105 ectodomain (ECD) and a p95 stub. As used herein, the term "p95" refers to the p95 portion of the HER-2 polypeptide produced after cleavage of the full-length HER-2 polypeptide (p185). Where the HER-2 is associated with a cell, the cleavage typically produces a p95 portion of the HER-2 polypeptide that remains associated with the cell while the ECD is released to the extracellular milieu. The term "ECD" refers to the p105 ectodomain (ECD) which is produced by the cleavage of the full-length HER-2 polypeptide (p185).

As previously discussed, p95 has been shown to interact with and potently activate signaling through EGFR (HER-1). Hence, increases in the cleavage of HER-2 will result in higher amounts of p95 which can potentially activate EGFR. Hence, in some embodiments, the MPI inhibits the activation of EGFR by inhibiting the cleavage of HER-2. As used herein, the term "EGFR" refers the epidermal growth factor receptor, a member of the ErbB family of receptors.

In some embodiments, the MPI inhibits HER-2 receptor-mediated signal transduction by inhibiting cleavage of HER-2 by the metalloprotease. In some embodiments, the aforementioned HER-2 receptor-mediated signal transduction is associated with a pathway selected from a mitogen activated protein (MAP) kinase pathway and a protein kinase B (AKT) and the MPI is ADAM10, ADAM15, or ADAM17 (see U.S. Patent Appl. No. 2004/0247602). In some embodiments, the aforementioned inhibition of HER-2 receptor-mediated signal transduction comprises inhibition of phosphorylation of a protein selected from an extracellular signal-regulated kinase (ERK) and a protein kinase B (AKT).

In some embodiments, the MPI inhibits the proteolytic activity of the metalloprotease. In some embodiments, the MPI inhibits the proteolytic activity of an ADAM. In some embodiments, the MPI inhibits the proteolytic activity of ADAM10, ADAM15, or ADAM17. In some embodiments, the MPI inhibits the proteolytic activity of ADAM 10.

In some embodiments, the MPI is a compound of Formula I:

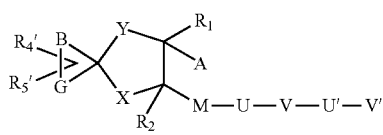

or a pharmaceutically acceptable salt thereof, wherein:

A is $CO_2H$, C(S)OH, C(O)NHOH, C(S)NHOH, C(O)N-HOR$_5$, C(S)NHOR$_5$, N(OH)CHO, N(OH)C(O)R$_6$, N(OH)C(S)R$_6$, SH, SR$_7$ or hydantoinyl;

B and G are each, independently, $(CH_2)_n$, $(CH_2)_nC(O)$, $(CH_2)_nC(S)$, $(CR_dR_f)_nNR_8$, $(CR_dR_f)_nO(CR_dR_f)_r$, $(CR_dR_f)_nS(CR_dR_f)_r$, $OC(O)NR_8$, $OC(S)NR_8$, O, $NR_8$, $S(O)_m$, S, $C(O)NR_8(CR_dR_f)_n$ or $C(O)(CR_dR_f)_n$;

X and Y are each, independently, absent, $(CH_2)_j$, $C_{1-10}$ alkylene substituted with 0 to 3 $R_a$, $C_{2-10}$ alkenylene substituted with 0 to 2 $R_a$, O, $NR_b$, $S(O)_m$, C=O, $NR_bC(O)$, $NR_bC(O)O$, $NR_bC(O)NR_b$, C(O)O, $NR_bS(O)_m$, $NR_bS(O)_mNR_b$ or $(CR_dR_f)_jNR_b$;

M is CO or $S(O)_i$;

U is absent, $C_{1-10}$ alkylene substituted with 0 to 5 $R_a$, $C_{2-10}$ alkenylene substituted with 0 to 2 $R_a$, O, $NR_b$, $NR_bC(O)$, $NR_bC(O)O$, $NR_bC(O)NR_b$, $NR_bS(O)_m$, or $NR_bS(O)NR_b$;

V is absent, $C_{3-13}$ carbocyclyl substituted with 0-5 $R_e$ or heterocyclyl substituted with 0-5 $R_e$;

U' is absent, $C_{1-10}$ alkylene substituted with 0 to 5 $R_a$, $C_{2-10}$ alkenylene substituted with 0 to 2 $R_a$, O, $NR_bS(O)_m$, C=O, $NR_bC(O)$, $NR_bC(O)O$, $NR_bC(O)NR_b$, C(O)O, O—($C_{1-10}$ alkylene) or $NR_bS(O)NR_b$;

V' is H, $C_{1-8}$ alkyl, $NR_bR_c$, $C_{3-13}$ carbocyclyl substituted with 0-5 $R_e$ or heterocyclyl substituted with 0-5 $R_e$;

$R_a$ and $R_e$ are each, independently, H, T, $C_{1-8}$ alkylene-T, $C_{2-8}$ alkenylene-T, $C_{2-6}$ alkynylene-T, $C(O)NR_a'(CR_b'R_c')_r$-T, $C(O)O(CR_b'R_c')_r$-T, $S(O)_p(CR_b'R_c')_r$-T, $(CR_b'R_c')_r$—O—$(CR_b'R_c')_r$-T, OH, Cl, F, Br, I, CN, $NO_2$, $NR^IR^{II}$, $COR^{III}$, $COOR^{IV}$, $OR^{IV}$, $CONR^IR^{II}$, $R^ICONR^IR^{II}$, $OCONR^IR^{II}$, $NR^ICOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, $C_{3-13}$ carbocyclyl, heterocyclyl, carbocyclylalkyl, or heterocyclylalkyl, wherein each of said carbocyclyl, heterocyclyl, carbocyclylalkyl, and heterocylcylalkyl groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

$R_b$ and $R_c$ are each, independently, H, T, $C_{1-6}$ alkylene-T, $C_{2-8}$ alkenylene-T, $C_{2-6}$ alkynylene-T, $C(O)NR_a'(CR_c'R_b')_r$-T, $C(O)O(CR_b'R_c')_r$-T, $C(O)(CR_b'R_c')_r$-T, $S(O)_p(CR_b'R_c')_r$-T, $(CR_c'R_b')_r$—O—$(CR_c'R_b')_r$-T, $C(NR_a'R_a')(=N-CN)$ or $C(NR_a'R_a')(=CHNO_2)$;

$R_d$ and $R_f$ are each, independently, H, $C_{1-6}$ alkyl, $C_{2-6}$ alkenyl, $C_{2-6}$ alkynyl, T, $C_{1-6}$ alkylene-T, $C_{2-8}$ alkenylene-T, $C_{2-6}$ alkynylene-T, $C(O)NR_a'(CR_c'R_b')_r$-T, $C(O)O(CR_b'R_c')_r$-T, $S(O)_p(CR_b'R_c')_r$-T, $(CR_c'R_b')_r$—O—$(CR_c'R_b')_r$-T, OH, Cl, F, Br, I, CN, $NO_2$, $NR^IR^{II}$, $COR^{III}$, $COOR^{IV}$, $OR^{IV}$, $CONR^IR^{II}$, $R^INCONR^IR^{II}$, $OCONR^IR^{II}$, $R^INCOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, carbocyclyl, heterocyclyl, carbocyclylalkyl, heterocyclylalkyl, carbocyclyloxy or heterocyclyloxy, wherein each of said carbocyclyl, heterocyclyl, carbocyclylalkyl, heterocyclylalkyl, carbocyclyloxy or heterocyclyloxy groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

T is H, $C_{1-10}$ alkyl substituted with 0 to 5 $R_b'$, $C_{2-10}$ alkenyl substituted with 0 to 5 $R_b'$, $C_{2-10}$ alkynyl substituted with 0 to 5 $R_b'$, $C_{1-6}$ alkoxy, $C_{3-13}$ carbocyclyl substituted with 0-3 $R_b'$, or heterocyclyl substituted with 0-5 $R_b'$;

$R_a'$, $R_b'$ and $R_c'$ are each, independently, H, $C_{1-6}$ alkyl, $C_{2-6}$ alkenyl, $C_{2-6}$ alkynyl, OH, Cl, F, Br, I, CN, $NO_2$, $NR^IR^{II}$, $COR^{III}$, $COOR^{IV}$, $OR^{IV}$, $CONR^IR^{II}$, $R^INCONR^IR^{II}$, $OCONR^IR^{II}$, $R^INCOR^{II}$, $SO_2NR^IR^{II}$, $NR^ISO_2R^{II}$, $NR^ISO_2NR^IR^{II}$, $OSO_2NR^IR^{II}$, $SO_pR^V$, $C_{1-8}$ haloalkyl, carbocyclyl, heterocyclyl, carbocyclylalkyl, heterocyclylalkyl, carbocyclyloxy or heterocyclyloxy, wherein each of said carbocyclyl, heterocyclyl, carbocyclylalkyl, heterocyclylalkyl, carbocyclyloxy or heterocyclyloxy groups is optionally substituted by one or more $C_{1-8}$ alkyl, alkoxy, halo, haloalkyl, haloalkoxy, cyano, nitro, amino, alkylamino, dialkylamino, carboxy, carboxy alkyl ester, carboxy aryl ester, aminocarbonyl, alkylaminocarbonyl, dialkylaminocarbonyl, sulfonyl, aminosulfonyl, alkylaminosulfonyl, dialkylaminosulfonyl, arylsulfonyl, arylsulfinyl, alkylsulfonyl or arylsufonyl;

$R_1$ and $R_2$ are each, independently, H, $C_{1-6}$ alkyl, $SR_{10}$, $OR_{10}$ or $NR_{11}R_{12}$;

$R_5$ is H, halogen, T, $C_{1-6}$ alkylene-T, $C_{2-6}$ alkynylene-T, $C(O)NR_a'(CR_c'R_b')_r$-T, $CO(CR_b'R_c')_r$-T, $C(O)O(CR_b'R_c')_r$-T, $S(O)_p(CR_b'R_c')_r$-T, $(CR_c'R_b')_r$—O—$(CR_c'R_b')_r$-T, $NR_{11}R_{12}$, $SR_{18}$ or $OR_{18}$;

$R_4'$ and $R_5'$ are each, independently, H, halogen, T, $C_{1-6}$ alkylene-T, $C_{2-6}$ alkynylene-T, $C(O)NR_a'(CR_c'R_b')_r$-T, $CO(CR_b'R_c')_r$-T, $C(O)O(CR_b'R_c')_r$-T, $S(O)_p(CR_b'R_c')_r$-T, $(CR_c'R_b')_r$—O—$(CR_c'R_b')_r$-T, $NR_{11}R_{12}$, $SR_{18}$, or $OR_{18}$;

or $R_4'$ and $R_5'$ together with the atoms to which they are attached form a ring selected from $C_{3-13}$ carbocyclyl and 3-14 membered heterocyclyl;

$R_6$ and $R_7$ are each, independently, H, $C_{1-6}$ alkyl, $C_{2-8}$ alkenyl or $C_{2-8}$ alkynyl;

$R_8$ is H, $C_{1-10}$ alkylene-T, $C_{2-10}$ alkenylene-T, $C_{2-10}$ alkynylene-T, $(CR_b'R_c')_rO(CR_b'R_c')_r$-T, $(CR_b'R_c')_rNR_a'(CR_b'R_c')_r$-T, $(CR_b'R_c')_rC(O)(CR_b'R_c')_r$-T, $(CR_b'R_c')_rC(O)O(CR_b'R_c')_r$-T, $(CR_b'R_c')_rOC(O)(CR_b'R_c')_r$-T, $(CR_b'R_c')_rC(O)NR_a'(CR_b'R_c')_r$-T, $(CR_b'R_c')_rNR_a'C(O)(CR_b'R_c')_r$-T, $(CR_b'R_c')_rOC(O)O(CR_b'R_c')_r$-T, $(CR_b'R_c')_rOC(O)NR_a'(CR_b'R_c')_r$-T, $(CR_b'R_c')_rNR_a'C(O)O(CR_b'R_c')_r$-T, $(CR_b'R_c')_rNR_a'C(O)NR_a'(CR_b'R_c')_r$-T, $(CR_b'R_c')_rS(O)_p(CR_b'R_c')_r$-T, $(CR_b'R_c')_rSO_2NR_a'(CR_b'R_c')_r$-T, $(CR_b'R_c')_rNR_a'SO_2(CR_b'R_c')_r$-T, or $(CR_b'R_c')_rSO_2NR_a'SO_2(CR_b'R_c')_r$-T;

$R_{10}$ is H or $C_1$-$C_6$alkyl;

$R_{11}$ and $R_{12}$ are each, independently, H or $C_1$-$C_8$ alkyl;

or $R_{11}$ and $R_{12}$ together with the N atom to which they are attached form a 3-14 member heterocyclic ring;

$R_{18}$ is $C_{1-6}$ alkyl;

$R^I$ and $R^{II}$ are each, independently, H, $C_{1-6}$ alkyl or $C_{3-13}$ carbocyclyl;

$R^{III}$ and $R^{IV}$ are each, independently, H, $C_{1-6}$ alkyl, haloalkyl, carbocyclyl, heterocyclyl, carbocyclylalkyl or heterocyclylalkyl, wherein said carbocyclyl, heterocyclyl, carbocyclylalkyl or heterocyclylalkyl are each optionally substituted by one or more halo, $C_{1-4}$ alkyl or $C_{1-4}$ alkoxy;

$R^V$ is $C_{1-6}$ alkyl, haloalkyl, carbocyclyl or heterocyclyl;

j is 1, 2, 3 or 4;
i is 0, 1 or 2;
n is 0, 1, 2, 3, 4, 5, 6, 7, 8, 9, 10, 11 or 12;
m is 0, 1 or 2;
p is 1 or 2; and
r is 0, 1, 2, 3, 4 or 5;
with the provisos:
a) the spiro ring is a stable chemical entity; and
b) $NR_g$ and $NR_b$ have no N—N or N—O bonds.

In some embodiments, A is C(O)NHOH.
In some embodiments, X is $(CR_dR_f)_jNR_b$ or $(CH_2)_j$.
In some embodiments, X is $(CH_2)_j$.
In some embodiments, X is $(CR_dR_f)_jNR_b$.
In some embodiments, X is $CH_2NR_b$, $CH_2CH_2$, or $CH_2$.
In some embodiments, X is $CH_2NR_b$.
In some embodiments, Y is $(CR_dR_f)_jNR_b$ or $(CH_2)_j$.
In some embodiments, Y is $(CH_2)_j$.
In some embodiments, Y is $(CR_dR_f)_jNR_b$.
In some embodiments, Y is $CH_2NR_b$, $CH_2CH_2$, or $CH_2$.
In some embodiments, Y is $CH_2$.
In some embodiments, B is $(CH_2)_n$.
In some embodiments, B is $CH_2$.
In some embodiments, G is $(CH_2)_n$.
In some embodiments, G is $CH_2$.
In some embodiments, U is absent or $NR_b$.
In some embodiments, U is absent.
In some embodiments, U' is absent, $C_{1-10}$ alkylene substituted with 0 to 5 $R_a$, O, C=O, or O—($C_{1-10}$ alkylene).
In some embodiments, U' is absent or $C_{1-10}$ alkylene substituted with 0 to 5 $R_a$.
In some embodiments, U' is absent.
In some embodiments, V is $C_{3-13}$ carbocyclyl substituted with 0-5 $R_e$ or heterocyclyl substituted with 0-5 $R_e$.
In some embodiments, V is heterocyclyl substituted with 0-5 $R_e$.
In some embodiments, V is heterocycloalkyl substituted with 0-5 $R_e$.
In some embodiments, V is 6-membered heterocycloalkyl substituted with 0-5 $R_e$.
In some embodiments, V is 6-membered heterocycloalkyl.
In some embodiments, V is piperazin-1,4-diyl, piperidin-1,3-diyl, piperidin-1,4-diyl, 3,6-dihydropyridin-1,4(2H)-diyl, azetidin-1,4-yl, pyrrolidin-1,3-diyl, 2,5-dihydro-1H-pyrrol-1,3-diyl, 2,3,4,7-tetrahydro-1H-azepin-1,5-diyl, azepan-1,4-diyl, or 2,3-dihydro-1H-indol-1,5-diyl.
In some embodiments, V is piperazin-1,4-diyl.
In some embodiments, V' is $C_{1-8}$ alkyl, $C_{3-13}$ carbocyclyl substituted with 0-5 $R_e$ or heterocyclyl substituted with 0-5 $R_e$.
In some embodiments, V' is $C_{3-13}$ carbocyclyl substituted with 0-5 $R_e$ or heterocyclyl substituted with 0-5 $R_e$.
In some embodiments, V' is heterocyclyl substituted with 0-5 $R_e$.
In some embodiments, V' is pyridin-2-yl, pyridin-3-yl, pyridin-4-yl, 5-(trifluoromethyl)pyridin-2-yl, 3-(trifluoromethyl)pyridin-2-yl, 4,7,-dihydrothieno[2,3-c]pyridine-6(5H)-yl, 3,4-dihydroisoquinolin-2-(1H)-yl, 2,3-dihydro-1H-indol-1-yl, 4-phenyl-1,3-thiazol-2-yl, 4-tert-butyl-1,3-thiazol-2-yl, 2-thienyl, 3-thienyl, dibenzo[b,d]furan-4-yl, 1-methyl-1H-benzimidazol-6-yl, 1-ethyl-1H-benzimidazol-6-yl, 1,3-benzothiazol-6-yl, 1,4,5,6-tetrahydrobenzo[f]isoquinolin-3(2H)-yl, 2,3-dihydrobenzofuran-5-yl, 3,3-dimethyl-2,3-dihydrobenzofuran-5-yl, pyrazin-2-yl, 1,3,4,9-tetrahydro-2H-β-carbolin 2-yl, 9-methyl-1,3,4,9-tetrahydro-2H-β-carbolin-2-yl, 3,4,10,10a-tetrahydropyrazino[1,2-a]indol-2(1H)-yl, quinolin-2-yl, quinolin-4-yl, 2-methyl-quinolin-4-yl, 3,3a,8,8a-tetrahydroindeno[1,2-c]pyrrol-2(1H)-yl, piperidin-1-yl, 1,4,4a,5,6,10b-hexahydrobenzo[f]isoquinolin-3-(2H)-yl, 1,3,3a,4,5,9b-hexahydro-2H-benzo[e]isoindol-2-yl, 1,2,4,4a,5,6-hexahydro-3H-pyrazino[1,2-a]quinolin-3-yl, 1-methyl-1H-indazol-5-yl, or 1,3-dihydro-1'H-spiro[indene-2,4'-piperdin]-1'-yl.

In some embodiments, V' is $C_{3-13}$ carbocyclyl substituted with 0-5 $R_e$.
In some embodiments, V' is aryl substituted with 0-5 $R_e$.
In some embodiments, V' is aryl.
In some embodiments, V' is phenyl, cyclohexyl, 2-naphthyl, or 5,6,7,8-tetrahydronaphthalen-2-yl.
In some embodiments, V' is phenyl substituted with 0-5 $R_e$.
In some embodiments, V' is phenyl.
In some embodiments, $R_e$ is H, T, $C_{1-8}$ alkylene-T, $(CR_b'R_c')_r$—O—$(CR_b'R_c')_r$-T, OH, Cl, F, Br, I, CN, $NO_2$, $NR^IR^{II}$, $COR^{III}$, $OR^{IV}$, $CONR^IR^{II}$, $C_{1-8}$ haloalkyl, $C_{3-13}$ carbocyclyl, or heterocyclyl.
In some embodiments, $R_b$ is H, T, $C_{1-6}$ alkylene-T, $C(O)O(CR_b'R_c')_r$-T, $C(O)(CR_b'R_c')_r$-T, or $S(O)_p(CR_b'R_c')_r$-T.
In some embodiments, $R_b$ is $C(O)O(CR_b'R_c')_r$-T.
In some embodiments, $R_b$ is $C(O)OCH_3$.
In some embodiments, $R_4'$ is H.
In some embodiments, $R_5'$ is H.
In some embodiments, $R_1$ is H.
In some embodiments, $R_2$ is H.
In some embodiments, j is 1.
In some embodiments, n is 1.
In some embodiments, r is 1.
In some embodiments, r is 0.
In some embodiments, T is H or methyl.
In some embodiments, T is H.
In some embodiments, T is methyl.
In some embodiments, the MPI is a compound of Formula I wherein:
A is C(O)NHOH;
B and G are each, independently, $(CH_2)_n$, $(CH_2)_nC(O)$, $(CH_2)_nC(S)$, $(CR_dR_f)_nNR_8$, $(CR_dR_f)_nO(CR_dR_f)_r$, $(CR_dR_f)_nS(CR_dR_f)_r$, $OC(O)NR_8$, O, $NR_8$, $S(O)_m$, S, $C(O)NR_8(CR_dR_f)_n$ or $C(O)(CR_dR_f)_n$;
X and Y are each, independently absent, $(CH_2)_j$, $C_{1-10}$ alkylene substituted with 0 to 3 $R_a$, $NR_b$, or $(CR_dR_f)_jNR_b$;
M is CO;
U is absent, $C_{1-10}$ alkylene substituted with 0 to 5 $R_a$, or $NR_b$;
V is absent, $C_{3-13}$ carbocyclyl substituted with 0-5 $R_e$ or heterocyclyl substituted with 0-5 $R_e$;
U' is absent, $C_{1-10}$ alkylene substituted with 0 to 5 $R_a$, O, $NR_bS(O)_m$, C=O, $NR_bC(O)$, $NR_bC(O)O$, $NR_bC(O)NR_b$, C(O)O, O—($C_1$-$C_{10}$ alkylene) or $NR_bS(O)NR_b$;
V' is H, $C_{1-8}$ alkyl, $NR_bR_c$, $C_{3-13}$ carbocyclyl substituted with 0-5 $R_e$ or heterocyclyl substituted with 0-5 $R_e$;
$R_e$ is H, T, $C_{1-8}$ alkylene-T, $(CR_b'R_c')_r$—O—$(CR_b'R_c')_r$-T, OH, Cl, F, Br, I, CN, $NO_2$, $NR^IR^{II}$, $COR^{III}$, $OR^{IV}$, $CONR^IR^{II}$, $C_{1-8}$ haloalkyl, $C_{3-13}$ carbocyclyl, or heterocyclyl;
$R_b$ and $R_c$ are each, independently, H, $C(O)O(CR_b'R_c')_r$-T or $S(O)_p(CR_b'R_e')_r$-T;
$R_d$ and $R_f$ are each, independently, H or $C_{1-6}$ alkyl;
$R_1$ and $R_2$ are each, independently H or $C_{1-6}$ alkyl; and
$R_4'$ and $R_5'$ are each, independently H, $C(O)NR_a'(CR_c'R_b')_r$-T, $C(O)O(CR_b'R_c')_r$-T or $S(O)_p(CR_b'R_c')_r$-T.

In some embodiments, the MPI is a compound of Formula I wherein:
A is C(O)NHOH;
B and G are each, independently, $(CH_2)_n$, $(CH_2)_nC(O)$, $(CR_dR_f)_nNR_8$, O, $NR_8$, $S(O)_m$, S, $C(O)NR_8(CR_dR_f)_n$ or $C(O)(CR_dR_f)_n$;

X and Y are each, independently, absent, $(CH_2)_j$, $CH_2NR_b$ or $CH_2CH_2NR_b$;

M is CO;

U is absent or $NR_b$;

V is heterocyclyl substituted with 0-5 $R_e$;

U' is absent, $C_{1-10}$ alkylene substituted with 0 to 5 $R_a$, or O;

V' is $NR_bR_c$, $C_{3-13}$ carbocyclyl substituted with 0-5 $R_e$ or heterocyclyl substituted with 0-5 $R_e$;

$R_e$ is H, T, OH, Cl, F, CN, or $C_{1-8}$haloalkyl;

$R_b$ is H, $C(O)NR_a'(CR_c'R_b')_r$-T, $C(O)O(CR_b'R_c')_r$-T, $C(O)(CR_b'R_c')_r$-T, $S(O)_p(CR_b'R_c')_r$-T, $(CR_c'R_b')_r$—O—$(CR_c'R_b')_r$-T, $C(NR_a'R_a')(=N-CN)$ or $C(NR_a'R_a')(=CHNO_2)$;

$R_c$ is H, T, $C_{1-6}$ alkylene-T, $C_{2-8}$ alkenylene-T or $C_{2-6}$ alkynylene-T;

$R_d$ and $R_f$ are each, independently, H or $C_{1-6}$ alkyl;

$R_a'$ is H or $C_{1-6}$ alkyl;

$R_b'$ and $R_c'$ are each, independently, H, $C_{1-6}$ alkyl, OH, Cl, F, Br, I, CN, $NO_2$, $NR^IR^{II}$, $OR^{IV}$ or $C_{1-8}$ haloalkyl;

$R_1$ and $R_2$ are each H;

$R_4'$ and $R_5'$ are each H;

j is 1 or 2;

n is 0, 1, 2, 3 or 4; and r is 0, 1 or 2.

In some embodiments, the MPI is a compound of Formula I wherein:

A is C(O)NHOH;

B and G are each $(CH_2)_n$;

X and Y are each, independently, absent, $(CH_2)_j$, $CH_2NR_b$ or $NR_bCH_2CH_2$;

M is CO;

U is absent;

V is heterocyclyl substituted with 0-5 $R_e$;

U' is absent, $C_{1-10}$ alkylene substituted with 0 to 5 $R_a$, or O;

V' is H, $C_{1-8}$ alkyl, $NR_bR_c$, $C_{3-13}$ carbocyclyl substituted with 0-5 $R_e$ or heterocyclyl substituted with 0-5 $R_e$;

$R_b$ is H, $C(O)NR_a'(CR_c'R_b')_r$-T, $C(O)O(CR_b'R_c')_r$-T, $C(O)(CR_b'R_c')_r$-T, $C(NR_a'R_a')(=N-CN)$ or $C(NR_a'R_a')(=CHNO_2)$;

$R_c$ is H, T, $C_{1-6}$ alkylene-T, $C_{2-8}$ alkenylene-T or $C_{2-6}$ alkynylene-T;

$R_a'$ is H or $C_{1-6}$ alkyl;

$R_b'$ and $R_c'$ are each, independently, H, $C_{1-6}$ alkyl, OH, Cl, F, Br, I, CN, $NO_2$, $NR^IR^{II}$, $OR^{IV}$ or $C_{1-8}$ haloalkyl;

$R_1$ and $R_2$ are each H;

$R_4'$ and $R_5'$ are each H;

j is 1 or 2;

n is 0, 1, 2, 3 or 4; and r is 0, 1 or 2.

In some embodiments, the MPI is a compound of Formula I wherein:

A is C(O)NHOH;

B and G are each $CH_2$;

X is $CH_2NR_b$;

Y is $CH_2$;

M is CO;

U and U' are each absent;

V is piperazin-1,4-diyl;

V' is phenyl;

$R_b$ is $C(O)O(CR_b'R_c')_r$-T;

$R_b'$, $R_c'$, $R_1$, $R_2$, $R_4'$, $R_5'$ and T are each H; and r is 1.

In some embodiments, the MPI is methyl (6S,7S)-7-[(hydroxyamino)carbonyl]-6-[(4-phenylpiperazin-1-yl)carbonyl]-5-azaspiro[2.5]octane-5-carboxylate or pharmaceutically acceptable salt thereof.

The above compounds of Formula I can be prepared according to the methods described in U.S. Patent App. Pub. No. 2004/0259896, which is incorporated herein by reference in its entirety.

At various places in the present specification, substituents of the compounds of Formula I are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

For compounds of the invention in which a variable appears more than once, each variable can be a different moiety selected from the Markush group defining the variable. For example, where a structure is described having two R groups that are simultaneously present on the same compound, the two R groups can represent different moieties selected from the Markush group defined for R.

At various places in the present specification, linking substituents are described. It is specifically intended that each linking substituent include both the forward and backward forms of the linking substituent. For example, $NR_b(CR_dR_f)_n$ includes both $NR_b(CR_dR_f)_n$ and $(CR_dR_f)_nNR_b$, $S(O)_mNR_b$ includes both $S(O)_mNR_b$ and $NR_bS(O)_m$, O—($C_1$-$C_{10}$ alkylene) includes both O—($C_1$-$C_{10}$ alkylene) and ($C_1$-$C_{10}$ alkylene)-O, and C(O)O includes both C(O)O and OC(O). Where the structure clearly requires a linking group, the Markush variables listed for that group are understood to be linking groups. For example, of the structure requires a linking group (e.g., U of Formula I) and the Markush group definition for that variable lists "alkyl," then it is understood that the "alkyl" represents a linking alkylene group.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "alkyl" is meant to refer to a saturated hydrocarbon group which is straight-chained or branched. Example alkyl groups include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments, an alkyl group can contain from 1 to about 20, from 2 to about 20, from 1 to about 10, from 1 to about 8, from 1 to about 6, from 1 to about 4, or from 1 to about 3 carbon atoms.

As used herein, the term "alkenyl" refers to an alkyl group having one or more double carbon-carbon bonds. Example alkenyl groups include ethenyl, propenyl, cyclohexenyl, and the like.

As used herein, the term "alkynyl" refers to an alkyl group having one or more triple carbon-carbon bonds. Example alkynyl groups include ethynyl, propynyl, and the like.

As used herein, the term "haloalkyl" refers to an alkyl group having one or more halogen substituents. As used herein, the term "haloalkyl" also refers to alkyl groups in which all of the hydrogen atoms are replaced with halogen atoms. Example haloalkyl groups include $CF_3$, $C_2F_5$, $CHF_2$, CCl₃, CHCl₂, C₂Cl₅, and the like. An alkyl group in which all of the hydrogen atoms are replaced with halogen atoms can also be referred to as "perhaloalkyl."

As used herein, the term "alkylene" or "alkylenyl" refers to a bivalent alkyl group. An example alkylene group is methylene or ethylene.

As used herein, the term "alkenylene" or "alkenylenyl" refers to a bivalent alkenyl group.

As used herein, the term "alkynylene" refers to a bivalent alkynyl group.

As used herein, "carbocyclyl" groups are saturated (i.e., containing no double or triple bonds) or unsaturated (i.e., containing one or more double or triple bonds) cyclic hydrocarbon moieties. Carbocyclyl groups can be mono- or polycyclic (e.g., having 2, 3 or 4 fused rings) or spirocyclic. Carbocyclyl groups can be aromatic (e.g., "aryl") or nonaromatic (e.g., "cycloalkyl"). Example carbocyclyl groups include cyclopropyl, cyclobutyl, cyclopentyl, cyclohexyl, cycloheptyl, cyclopentenyl, 1,3-cyclopentadienyl, cyclohexenyl, norbornyl, norpinyl, norcarnyl, adamantyl, phenyl, and the like. In some embodiments, carbocyclyl groups can have from about 3 to about 30 carbon atoms, about 3 to about 20, about 3 to about 10, or about 3 to about 7 carbon atoms.

As used herein, the term "aryl" refers to an aromatic carbocyclyl group including monocyclic or polycyclic (e.g., having 2, 3 or 4 fused rings) aromatic hydrocarbons such as, for example, phenyl, naphthyl, anthracenyl, phenanthrenyl, indanyl, indenyl, and the like. In some embodiments, aryl groups have from 6 to about 20 carbon atoms.

As used herein, "cycloalkyl" refers to non-aromatic carbocyclyl groups including cyclized alkyl, alkenyl, and alkynyl groups. Cycloalkyl groups can include bi- or polycyclic (e.g., having 2, 3 or 4 fused rings) ring systems as well as spiro ring systems. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, adamantyl, and the like. Also included in the definition of cycloalkyl are moieties that have one or more aromatic rings fused (i.e., having a bond in common with) to the cycloalkyl ring, for example, benzo derivatives of pentane, pentene, hexane, and the like.

As used herein, "heterocyclyl" or "heterocycle" refers to a saturated or unsaturated cyclic group wherein one or more of the ring-forming atoms of the is a heteroatom such as oxygen, sulfur, or nitrogen. Heterocyclyl groups can be aromatic (e.g., "heteroaryl") or non-aromatic (e.g., "heterocycloalkyl"). Heterocyclyl groups can also correspond to hydrogenated and partially hydrogenated heteroaryl groups. Heterocyclyl groups can include mono- or polycyclic (e.g., having 2, 3 or 4 fused rings) ring systems. Heterocyclyl groups can be characterized as having 3-20 ring-forming atoms. In some embodiments, heterocyclyl groups can contain, in addition to at least one heteroatom, from about 1 to about 20, about 2 to about 10, or about 2 to about 7 carbon atoms and can be attached through a carbon atom or heteroatom. In further embodiments, the carbon atoms or hetereoatoms in the heterocyclyl or heterocycle ring can be oxidized (to form, e.g., a carbonyl, sulfinyl, sulfonyl, or other oxidized nitrogen or sulfur linkage) or a nitrogen atom can be quaternized. Examples of heterocyclyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like, as well as any of the groups listed below for "heteroaryl" and "heterocycloalkyl." Further example heterocycles include pyrimidinyl, phenanthridinyl, phenanthrolinyl, phenazinyl, phenothiazinyl, phenoxathiinyl, phenoxazinyl, phthalazinyl, piperazinyl, piperidinyl, 3,6-dihydropyridyl, 1,2,3,6-tetrahydropyridyl, 1,2,5,6-tetrahydropyridyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, tetrahydrofuranyl, tetrahydroisoquinolinyl, tetrahydroquinolinyl, tetrazolyl, 6H-1,2,5-thia-diazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, octahydro-isoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, quinazolinyl, quinolinyl, 4H-quinolizinyl, quinoxalinyl, quinuclidinyl, acridinyl, azocinyl, benzimidazolyl, benzofuranyl, benzothiofuranyl, benzo-thiophenyl, benzoxazolyl, benzthiazolyl, benztriazolyl, benztetrazolyl, benzisoxazolyl, benzisothiazolyl, benzimidazolinyl, methylenedioxyphenyl, morpholinyl, naphthyridinyl, decahydroquinolinyl, 2H,6H-1,5,2dithiazinyl, dihydrofuro[2,3-b]tetrahydrofuran, furanyl, furazanyl, carbazolyl, 4aH-carbazolyl, carbolinyl, chromanyl, chromenyl, cinnolinyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl and isoxazolyl. Further examples of heterocyclyl groups and heterocycles include pyridin-2-yl, pyridin-3-yl, pyridin-4-yl, 5-(trifluoromethyl)pyridin-2-yl, 3-(trifluoromethyl)pyridin-2-yl, 4,7,-dihydrothieno[2,3-c]pyridine-6(5H)-yl, 3,4-dihydroisoquinolin-2-(1H)-yl, 2,3-dihydro-1H-indol-1-yl, 4-phenyl-1,3-thiazol-2-yl, 4-tert-butyl-1,3-thiazol-2-yl, 2-thienyl, 3-thienyl, dibenzo[b,d]furan-4-yl, 1-methyl-1H-benzimidazol-6-yl, 1-ethyl-1H-benzimidazol-6-yl, 1,3-benzothiazol-6-yl, 1,4,5,6-tetrahydrobenzo[f]isoquinolin-3(2H)-yl, 2,3-dihydrobenzofuran-5-yl, 3,3-dimethyl-2,3-dihydrobenzofuran-5-yl pyrazin-2-yl, 1,3,4,9-tetrahydro-2H-β-carbolin-2-yl, 9-methyl-1,3,4,9-tetrahydro-2H-β-carbolin-2-yl, 3,4,10,10a-tetrahydropyrazino[1,2-a]-indol-2(1H)-yl, quinolin-2-yl, quinolin-4-yl, 2-methyl-quinolin-4-yl, 3,3a,8,8a-tetrahydroindeno[1,2-c]pyrrol-2(1H)-yl, piperidin-1-yl, 1,4,4a,5,6,10b-hexahydrobenzo[f]isoquinolin-3-(2H)-yl, 1,3,3a,4,5,9b-hexahydro-2H-benzo[e]isoindol-2-yl, 1,2,4,4a,5,6-hexahydro-3H-pyrazino[1,2-a]quinolin-3-yl, 1-methyl-1H-indazol-5-yl, and 1,3-dihydro-1'H-spiro[indene-2,4'-piperdin]-1'-yl groups. Further example heterocyclyl groups and heterocycles include piperazin-1,4-diyl, piperidin-1,3-diyl, piperidin-1,4-diyl, 3,6-dihydropyridin-1,4(2H)-diyl, azetidin-1,4-yl, pyrrolidin-1,3-diyl, 2,5-dihydro-1H-pyrrol-1,3-diyl, 2,3,4,7-tetrahydro-1H-azepin-1,5-diyl, azepan-1,4-diyl, and 2,3-dihydro-1H-indol-1,5-diyl groups. Heterocyclyl groups and heterocycles also include fused ring and spiro compounds containing, for example, the above heterocycles.

As used herein, the term "heteroaryl" groups are aromatic heterocyclyl groups and include monocyclic and polycyclic (e.g., having 2, 3 or 4 fused rings) aromatic hydrocarbons that have at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrryl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, benzothienyl, purinyl, carbazolyl, benzimidazolyl, indolinyl, and the like. In some embodiments, the heteroaryl group has from 1 to about 20 carbon atoms, and in further embodiments from about 3 to about 20 carbon atoms. In some embodiments, the heteroaryl group contains 3 to about 14, 3 to about 7, or 5 to 6 ring-forming atoms. In some embodiments, the heteroaryl group has 1 to about 4, 1 to about 3, or 1 to 2 heteroatoms.

As used herein, the term "heterocycloalkyl" refers to non-aromatic heterocyclyl groups including cyclized alkyl, alkenyl, and alkynyl groups that have at least one heteroatom ring member such as nitrogen, oxygen, or sulfur. In some embodiments, the carbon atoms or heteroatoms in the heterocycloalkyl group can be oxidized (to form, e.g., a carbonyl, sulfinyl, sulfonyl, etc.) or a nitrogen atom can be quaternized. Example heterocycloalkyl groups include morpholino, thiomorpholino, piperazinyl, tetrahydrofuranyl, tetrahydrothienyl, 2,3-dihydrobenzofuryl, 1,3-benzodioxole, benzo-1,4-dioxane, piperidinyl, pyrrolidinyl, isoxazolidinyl, isothiazolidinyl, pyrazolidinyl, oxazolidinyl, thiazolidinyl, imidazolidinyl, and the like. Also included in the definition of heterocycloalkyl are moieties that have one or more aromatic rings fused (i.e., having a bond in common with) to the non-aromatic heterocyclic ring, for example phthalimidyl, naphthalimidyl, and benzo derivatives of heterocycles such as indolene and isoindolene groups. In some embodiments, the heterocycloalkyl group has from 1 to about 20 carbon atoms, and in further embodiments from about 3 to about 20 carbon atoms. In some embodiments, the heterocycloalkyl group contains 3 to about 14, 3 to about 7, or 5 to 6 ring-forming atoms. In some embodiments, the heterocycloalkyl group has 1 to about 4, 1 to about 3, or 1 to 2 heteroatoms. In some embodiments, the heterocycloalkyl group contains 0 to 3 double bonds. In some embodiments, the heterocycloalkyl group contains 0 to 2 triple bonds.

As used herein, the terms "halo" or "halogen" refer to a fluorine, chlorine, bromine, or iodine atom.

As used herein, the term "alkoxy" refers to an —O-alkyl group. Example alkoxy groups include methoxy, ethoxy, n-propoxy, isopropoxy, n-butoxy, tert-butoxy, and the like.

As used herein, the term "aryloxy" refers to an —O-aryl group. An example aryloxy group is phenoxy.

As used here, the term "haloalkoxy" refers to an —O-haloalkyl group. An example haloalkoxy group is $OCF_3$.

As used herein, the term "carbocyclyloxy" refers to an —O-carbocyclyl group. Example carbocyclyloxy groups are cyclohexoxy and phenoxy.

As used herein, the term "heterocyclyloxy" refers to an —O-heterocyclyl group. An example heterocycyl groups is pyridin-4-yl-oxy.

As used herein, the term "carbocyclylalkyl" refers to an alkyl moiety substituted by a carbocyclyl group. Example carbocyclylalkyl groups include "aralkyl" (alkyl substituted by aryl ("arylalkyl")) and "cycloalkylalkyl" (alkyl substituted by cycloalkyl). In some embodiments, carbocyclylalkyl groups have from 4 to 24 carbon atoms.

As used herein, the term "heterocyclylalkyl" refers to an alkyl moiety substituted by a heterocyclyl group. Example heterocyclylalkyl groups include "heteroarylalkyl" (alkyl substituted by heteroaryl) and "heterocycloalkylalkyl" (alkyl substituted by heterocycloalkyl). In some embodiments, heterocyclylalkyl groups have from 3 to 24 carbon atoms in addition to at least one heteroatom ring member, such as oxygen, nitrogen, or sulfur As used herein, the term "amino" refers to an $NH_2$ group. The term "alkylamino" refers to an amino group substituted by an alkyl group, and the term "dialkylamino" refers to an amino group substituted by two alkyl groups.

As used herein, the term "aminocarbonyl" refers to $CONH_2$.

As used herein, the term "alkylaminocarbonyl" refers to CONH(alkyl).

As used herein, the term "dialkylaminocarbonyl" refers to $CON(alkyl)_2$.

As used herein, the term "carboxy" or "carboxyl" refers to COOH.

As used herein, the term "carboxy alkyl ester" refers to COO-alkyl.

As used herein, the term "carboxy aryl ester" refers to COO-aryl.

As used herein, the term "cyano" refers to CN, where the carbon and nitrogen atoms are triply bonded to each other.

As used herein, the term "hydroxy" refers to OH

As used herein, the term "mercapto" refers to SH.

As used herein, the term "nitro" refers to $NO_2$.

As used herein, the term "sulfinyl" refers to SO.

As used herein, the term "sulfonyl" refers to $SO_2$.

As used herein, the term "aminosulfonyl" refers to $SO_2NH_2$.

As used herein, the term "alkylaminosulfonyl" refers to $SO_2NH(alkyl)$.

As used herein, the term "dialkylaminosulfonyl" refers to $SO_2N(alkyl)_2$.

As used herein, the term "arylsulfonyl" refers to $SO_2$-aryl.

As used herein, the term "arylsulfinyl" refers to SO-aryl.

As used herein, the term "alkylsulfonyl" refers to $SO_2$-alkyl.

As used herein, the term "alkylsulfinyl" refers to SO-alkyl.

Unless otherwise indicated, the compounds of Formula I are meant to include pharmaceutically acceptable salts, prodrugs, enantiomers, diastereomers, racemic mixtures, crystalline forms, non-crystalline forms, amorphous forms, hydrates and solvates thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable risk/benefit ratio.

The present invention also includes pharmaceutically acceptable salts of the compounds of Formula I. As used herein, "pharmaceutically acceptable salts" refers to derivatives of the disclosed compounds wherein the parent compound is modified by converting an existing acid or base moiety to its salt form. Certain specific compounds of Formula I may contain both basic and acidic functionalities that allow the compounds to be converted into either base or acid addition salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts or the quaternary ammonium salts of a parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The compounds of Formula I can possess chiral or asymmetric carbon atoms (e.g., having one or more stereocenters); the racemates, diastereomers, enantiomers, and individual optical isomers are all intended to be encompassed within the scope of the present invention, unless otherwise indicated. Compounds of Formula I that contain asymmetrically substituted carbon atoms can be isolated in optically active or racemic forms. Methods on how to prepare optically active forms from optically active starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. The compounds of Formula I can also include cis and trans geometric isomers which may be isolated as a mixture of isomers or as separated isomeric forms.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of Formula I also include tautomeric forms, such as keto-enol tautomers. Tautomeric forms can be in equilibrium or sterically locked into one form by appropriate substitution.

Some of the compounds of Formula I can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention. Compounds of Formula I further include anhydrous and non-solvated forms.

Compounds of Formula I can also include all isotopes of atoms occurring in the intermediates or final compounds. Isotopes include those atoms having the same atomic number but different mass numbers. For example, isotopes of hydrogen include tritium and deuterium.

In addition to salt forms, the present invention also includes prodrugs of the compounds of Formula I. As used herein, the term "prodrugs" refer to any covalently bonded carriers which release the active parent drug when administered to a patient. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a patient, cleaves to form a free hydroxyl, amino, sulfhydryl, or carboxyl group respectively. Examples of prodrugs include, but are not limited to, acetate, formate and benzoate derivatives of alcohol and amine functional groups in the compounds of the invention. Preparation and use of prodrugs is discussed in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference in their entireties. Additionally, prodrugs can be converted to the compounds of the present invention by chemical or biochemical methods in an ex-vivo environment. For example, prodrugs can be slowly converted to the compounds of Formula I when placed in a transdermal patch reservoir with a suitable enzyme or chemical reagent.

The MPIs of Formula I can be synthesized as summarized for the Formula I and II compounds of U.S. Patent Appl. No. 2004/0259896, which is incorporated herein by reference in its entirety. The compounds of Formula I of the present invention can also be prepared by a variety of methods known to one skilled in the art of organic synthesis, as well as by variations on such methods as appreciated by those skilled in the art.

As used herein, the term "hormone therapy" refers methods for inhibiting or counteracting the effect of class X hormones on the growth and/or survival of cancerous cells in the patients with various types of cancers. As used herein, the term "class X hormones" refers to the hormones which bind to and activate class X hormone receptors. As used herein, the term "class X hormones" also refers to hormones which can participate in the regulation of cancer cell growth and/or survival. As used herein, the term "class X hormone receptors" refers to receptors which can participate in the regulation of cancer cell growth and/or survival. Class X hormones include, but are not limited to, estrogens and androgens. Such class X hormone receptors include, but are not limited to, the estrogen or androgen receptors. Any reference herein to the estrogen or androgen receptor is meant to encompass all estrogen and androgen receptors. Such estrogens include, but are not limited to estradiol and estrone. Such androgens include but are not limited to testosterone and dihydroxytestosterone. The hormone therapies useful in the present invention may be chosen to target one type of class X hormone only or can be chosen to target several types of class X hormones simultaneously, depending on the type, presentation, and progression of the cancer.

As used herein, "hormone therapy" also refers to methods for inhibiting or eliminating the production of class X hormones, either directly or indirectly. Such methods include surgical methods that remove all or part of the organs or glands which participate in the production of class X hormones. Such organs and glands include the ovaries, the testicles, the adrenal gland, and the pituitary gland. Hence, in one embodiment, hormone therapy refers oophorectomy (the removal of the ovaries), orchiectomy (the removal of the testicles), adrenalectomy (the removal of the adrenal gland), and hypophysectomy (the removal of the pituitary gland). The hormone therapies of the present invention include both bilateral orchiectomy, where each testicle is removed in its entirety, and subcapsular orchiectomy, where the contents of each testicle are removed and the outer shell of the testicle is left in place.

The hormone therapies of the present invention also include radiation treatment, in which the organs or glands of the patient are subjected to radiation in an amount sufficient to inhibit or eliminate the production of the targeted class X hormones. For example, the ovaries of a female patient or the testicles of a male patient can be subjected to radiation in order to inhibit or eliminate the production of estrogen or androgen compounds, respectively.

Other useful hormone therapies include the administration of a therapeutically effective amount of a hormone therapy agent. As used herein, the term "hormone therapy agent" refers to a compound or substance that inhibits or counteracts the effect of class X hormones on the growth and/or survival of cancerous cells in the patients with various types of cancers. As used herein, the term "hormone therapy agent" also refers to a compound or substance that inhibits or eliminates the production of class X hormones, either directly or indirectly. As used herein, the term "compound" refers to any small molecule, whether organic or inorganic. As used herein, the term "substance" refers to a peptide, polymer, protein, antibody, enzyme, and the like.

The specific type of hormone therapy chosen depends on a variety of factors, including the type of the cancer. For example, hormone therapy for breast cancer can attempt to inhibit or counteract the effect of estrogens on the growth of cancer cells, while hormone therapy for prostate cancer can attempt to inhibit or counteract the effect of androgens on the growth of cancer cells. Besides the type of cancer, a skilled practitioner will choose the appropriate hormone therapy based on a variety of other factors as well, including the type of receptors expressed by the cancer cells. Hence, a cancer expressing the estrogen receptor will likely respond best to hormone therapies which target the estrogen class X hormone. In the present invention, therefore, the hormone therapy may be chosen to counteract or inhibit the effect of only one type of class X hormone (e.g., estrogen for breast cancer or androgens for prostate cancer). In such a case, the hormone therapy can include the administration of other non-targeted class X hormones. For example, a patient in need of treatment for prostate cancer might be treated with estrogens or a patient of treatment for breast cancer might be treated with androgens. Alternatively, the hormone therapy may be chosen to target the effect of several different types of class X hormones at once. For example, a patient in need of treatment for breast cancer or prostate cancer may receive hormone therapy which targets both androgens and estrogens depending on the progression and presentation of the pathology.

In some embodiments, the hormone therapy includes administering to the patient a therapeutically effective amount of at least one hormone therapy agent.

In some embodiments, the hormone therapy includes administering to a patient a therapeutically effective amount of at least one compound selected from a selective estrogen receptor modulator, estrogen receptor downregulator, aromatase inhibitor, luteinizing hormone-releasing hormone analogue, gonadotrophin-releasing hormone antagonist, progestational agent, adrenocorticosteroid, somatostatin analogue, estrogen, androgen, anti-estrogen agent, androgen receptor blocking agent, anti-androgen agent, 5-alpha reductase inhibitor, adrenal production inhibitor, and other hormone therapy agent.

In some embodiments, the hormone therapy includes administering to said patient a therapeutically effective amount of at least one selective estrogen receptor modulator. As used herein, the term "selective estrogen receptor modulator" is a compound or substance that binds to the estrogen receptor and partially blocks its function (Schiff & Osborne, Breast Cancer Res. 7, 205-211 (2005)). In some embodiments, the selective estrogen receptor modulator is tamoxifen, raloxifene, toremifen, trioxifene, keoxifene, 4-hydroxytamoxifene, CC-8490, or black cohosh.

In some embodiments, the hormone therapy includes administering to the patient a therapeutically effective amount of at least one estrogen receptor downregulator. As used herein, the term "estrogen receptor downregulator" refers to a compound or substance which downregulates the estrogen receptor, by binding to the receptor and acting as an antagonist, by deforming the receptor, or by destroying the receptor. In some embodiments, the estrogen receptor downregulator is fulvestrant.

In some embodiments, the hormone therapy includes administering to the patient a therapeutically effective amount of at least one aromatase inhibitor. As used herein, the term "aromatase inhibitor" refers to a compound or substance which inhibits the conversion of androgen to estrogen in peripheral tissues. In some embodiments, the aromatase inhibitor is anastrozole, exemestane, vorozole, aminoglutethimide, formestane, testolactone, fadrazole, or letrozole.

In some embodiments, the hormone therapy includes administering to the patient a therapeutically effective amount of at least one lutenizing hormone-releasing hormone analogue. As used herein, the term "lutenizing hormone-releasing hormone analogue" refers to an analogue to lutenizing hormone-releasing hormone that binds to the receptors in the gonadotrophs, thereby blocking the release of lutenizing hormone and follicle-stimulating hormone, which in turn inhibits the production of estrogen, testosterone, and progesterone. Lutenizing hormone-releasing hormone (also known as gonadotrophin-releasing hormone) is a peptide that is synthesized and secreted from hypothalamus neurons. It binds to receptors on the gonadotrophs and stimulates the production of lutenizing hormone and follicle-stimulating hormone. These two hormones can stimulate the production of estrogen, testosterone, and progesterone. A lutenizing hormone-releasing hormone analogue binds to the receptors in the gonadotrophs in a similar manner to the lutenizing hormone-releasing hormone, displaying agonist activity. While the lutenizing hormone-releasing hormone analogue initially stimulates production of lutenizing hormone and follicle-stimulating hormone, it eventually blocks release of these hormones, thereby reducing the amount of estrogen, testosterone or progesterone. In some embodiments, the lutenizing hormone-releasing hormone analogue is buserelin, deslorelin, leuprolide, leuprolide acetate, goserelin, nafarelin, goserelin acetate, triptorelin acetate, histrelin, or triptorelin.

In some embodiments, the hormone therapy includes administering to the patient a therapeutically effective amount of at least one gonadotrophin-releasing hormone antagonist. As used herein, the term "gonadotrophin-releasing hormone antagonist" refers to a compound or substance which binds to the receptors in the gonadotrophs and displays antagonist activity, thereby inhibiting or eliminating the production of lutenizing hormone and follicle-stimulating hormone, which in turn inhibits production of estrogen, testosterone, and progesterone. In some embodiments, the gonadotrophin-releasing hormone antagonist is antarelix, cetrorelix, degarelix, or abarelix.

In some embodiments, the hormone therapy includes administering to the patient a therapeutically effective amount of at least one progestational agent. As used herein, the term "progestational agent" refers to progestagens and progestins. While not wishing to be bound by any particular theory, progestational agents appear to function by downregulating certain class X receptors, such as the estrogen receptor, or to suppress the effect of estrogens and androgens. In some embodiments, the progestational agent is acetoxypregnenolone, allylestrenol, anagestone acetate, chlormadinone acetate, cyproterone, cyproterone acetate, desogestrel, dihydrogesterone, dimethisterone, ethisterone, ethynodiol diacetate, flurogestone acetate, gestodene, hydroxyprogesterone, hydroxyprogesterone acetate, hydroxyprogesterone caproate, hydroxymethylprogesterone, hydroxymethylprogesterone acetate, 3-ketodesogestrel, levonorgestrel, lynestrenol, medrogestone, medroxyprogesterone acetate, megestrol, megestrol acetate, melengestrol acetate, norethindrone, norethindrone acetate, norethisterone, norethisterone acetate, norethynodrel, norgestimate, norgestrel, norgestrienone, normethisterone, progesterone, dienogest, drospirenone, nomegestrol acetate, hydroxyprogesterone, or trimegestone.

In some embodiments, the hormone therapy includes administering to the patient a therapeutically effective amount of at least one adrenocorticosteroid. While not wishing to be bound by any one theory, adrenal cortiosteroids appear to suppress estrogen production by the adrenal cortex. In some embodiments, the adrenocorticosteroid is dexathasone, prednisone, or methylprednisone.

In some embodiments, the hormone therapy includes administering to the patient a therapeutically effective amount of at least one somatostatin analogue. As used herein, the term "somatostatin analogue" refers to a compound or substance analogous to somatostatin, which can suppress the secretion of lutenizing hormone, which can in turn inhibit the production of class X hormones. In addition, somatostatin receptors are frequently expressed in many types of cancers, including lymphomas, breast, and small-cell lung cancers. In some embodiments, the somastatin analogue is octreotide or lanreotide.

In some embodiments, the hormone therapy includes administering to the patient a therapeutically effective amount of at least one estrogen. In some embodiments, estrogens can be used to treat cancer whose growth is sensitive to androgens, since they can inhibit androgen secretion. In some embodiments, the estrogen is estradiol, estradiol benzoate, estradiol valerate, estriadiol cypionate, estradiol heptanoate, estradiol decanoate, estradiol acetate, estradiol diacetate, 17α-estradiol, ethynylestradiol, ethynylestradiol 3-acetate, ethynylestradiol 3-benzoate, ethinyl estradiol, estriol, estriol succinate, polyestrol phosphate, estrone, estrone acetate, estrone sulfate, piperazine estrone sulfate, quinestrol, mestranol, a conjugated equine estrogen, diethylstilbestrol, or other pharmaceutically acceptable ester or ether thereof.

In some embodiments, the hormone therapy comprises administering to said patient a therapeutically effective amount of at least one androgen. In some embodiments, androgens can be used to treat cancer whose growth is sensitive to estrogens, since they can inhibit the secretion of estrogens. In some embodiments, the androgen is androsterone, androsterone acetate, androsterone propionate, androsterone benzoate, androstenediol, androstenediol-3-acetate, androstenediol-17-acetate, androstenediol-3,17-diacetate, androstenediol-17-benzoate, androstenediol-3-acetate-17-benzoate, androstenedione, dehydroepiandrosterone, sodium dehydroepiandrosterone sulfate, 4-dihydrotestosterone, 5α-dihydrotestosterone, dromostanolone, dromostanolone propionate, ethylestrenol, nandrolone phenpropionate, nandrolone decanoate, nandrolone furylpropionate, nandrolone cyclohexanepropionate, nandrolone benzoate, nandrolone cyclohexanecarboxylate, oxandrolone, stanozolol, testosterone, testolactone, calusterone, fluoxynesterone, or pharmaceutically acceptable esters of testosterone and 4-dihydrotestosterone.

In some embodiments, the hormone therapy includes administering to the patient a therapeutically effective amount of at least one anti-estrogen agent. As used herein, an anti-estrogen agent refers to a compound or substance which inhibits or counteracts the effect of estrogen on cancer cell growth and/or survival, or that inhibits or eliminates, either directly or indirectly, the production of estrogen. Thus, as used herein, the term "anti-estrogen agent" encompasses many of the other types of hormone therapy agents mentioned herein. For example, anti-estrogen agents include, but are not limited to, selective estrogen receptor modulators, aromatase inhibitors, luteinizing hormone-releasing hormones, gonadotrophin releasing hormone antagonists, somatostatin analogues, and androgens. As used herein, the term "anti-estrogen agent" also includes other types of hormone therapy agents that can inhibit or counteract the effect of estrogen on cancer cell growth and/or survival, or that inhibit or eliminate, either directly or indirectly, the production of estrogen, that are not recited herein, but that are known to one of ordinary skill in the art now or will become known to one of ordinary skill in the future.

In some embodiments, the hormone therapy includes administering to the patient a therapeutically effective amount of at least one androgen receptor blocking agent. As used herein, the term "androgen receptor blocking agent" refers to a compound or substance that binds to androgen receptors and interferes with ability of androgens to regulate cancer cell growth and/or survival. In some embodiments, the androgen receptor blocking agent is a compound and substance that binds to androgen receptors and interferes with the ability of testosterone or dihydroxytesterone to regulate cell growth and/or survival. In some embodiments, said androgen receptor blocking agent is bicalutamide, cyproterone, cyproterone acetate, flutamide, or nilutamide.

In some embodiments, the hormone therapy includes administering to the patient a therapeutically effective amount of at least one anti-androgen agent. As used herein, the term "anti-androgen agent" refers to a compound or substance inhibits or counteracts the effect of androgens on cancer cell growth and/or survival, or that inhibits or eliminates the production of androgens. Thus, as used herein, the term "anti-androgen agent" encompasses many of the other types of hormone therapy agents mentioned herein. For example, anti-androgen agents include, but are not limited to, androgen receptor blocking agents, luteinizing hormone-releasing hormones, gonadotrophin releasing hormone antagonists, somatostatin analogues, 4-alpha reductase inhibitors, adrenal production inhibitors, and estrogens. As used herein, the term "anti-androgen agent" also includes types of hormone therapy agents that can inhibit or counteract the effect of androgens on cancer cell growth and/or survival, or that inhibit or eliminate, either directly or indirectly, the production of androgens, that are not recited herein, but that are known to one of ordinary skill in the art now or will become known to one of ordinary skill in the future.

In some embodiments, the hormone therapy includes administering to the patient a therapeutically effective amount of at least one 5-alpha reductase inhibitor. As used herein, the term "5-alpha reductase inhibitor" refers to a compound or substance that inhibits the enzyme 5-alpha reductase which is responsible for converting testosterone to dihydroxytestosterone. Dihydroxytesterone can bind to one of the androgen receptors. In some embodiments, the 5-alpha reductase inhibitor is finasteride or dutasteride.

In some embodiments, the hormone therapy includes administering to the patient a therapeutically effective amount of at least one adrenal production inhibitor. As used herein, the term "adrenal production inhibitor" refers to a compound or substance that inhibits the function of the adrenal glands. In some embodiments, the adrenal production inhibitor inhibits or eliminates the production of androgens by the adrenal glands. Approximately 10% of circulating androgens is produced by the adrenal glands. In some embodiments, the adrenal production inhibitor is ketoconazole, mitotane, or metyrapone.

In some embodiments, the hormone therapy includes administering to the patient a therapeutically effective amount of at least one other hormone therapy agent. As used herein, the term "other hormone therapy agent" refers to any hormone therapy agent that is not described specifically herein but which inhibits or counteracts the effect of any class X hormone on the growth and/or survival of cancer cells or that inhibits or eliminates the production of any class X hormone.

The hormone therapy agents of the present invention include pharmaceutically acceptable salts, prodrugs, hydrates, amorphous forms, and solvates thereof.

In some embodiments, the hormone therapy comprises exposing the organs or glands of the patient to a therapeutically effective amount of radiation.

In some embodiments, the hormone therapy comprises exposing the ovaries or testicles of the patient to a therapeutically effective amount of radiation.

In some embodiments, the hormone therapy is oophorectomy, orchiectomy, adrenectomy, or hypopysectomy.

In some embodiments, said hormone therapy agent is an anti-androgen agent, but not an androgen receptor blocking agent.

In some embodiments, said hormone therapy agent is an anti-androgen agent, but not bicalutamide.

In some embodiments, the hormone therapy agent is an androgen receptor blocking agent, but not bicalutamide.

In some embodiments, the hormone therapy agent is an anti-estrogen agent, but not a selective estrogen receptor modulator.

In some embodiments, the hormone therapy agent is an anti-estrogen agent, but not tamoxifen.

In some embodiments, the hormone therapy agent is a selective estrogen receptor modulator, but not tamoxifen.

In some embodiments, the hormone therapy comprises administering to said patient a therapeutically effective amount of a hormone therapy agent, wherein said hormone therapy agent is not tamoxifen.

In some embodiments, the hormone therapy comprises administering to said patient a therapeutically effective amount of a hormone therapy agent, wherein said hormone therapy agent is not a selective estrogen receptor modulator.

In some embodiments, the hormone therapy comprises administering to said patient a therapeutically effective amount of a hormone therapy agent, wherein said hormone therapy agent is not bicalutamide.

In some embodiments, the hormone therapy comprises administering to said patient a therapeutically effective amount of a hormone therapy agent, wherein said hormone therapy agent is not an androgen receptor blocking agent.

In some embodiments, the method of treating cancer further includes administering to a patient a EGFR tyrosine kinase inhibitor. As used herein, the term "tyrosine kinase" refers to an enzyme that catalyzes phosphorylation of tyrosine residues in proteins. As used herein, the term "EGFR tyrosine kinase inhibitor" refers to a compound or substance that inhibits the catalytic activity of the EGFR tyrosine kinase. Example EGFR tyrosine kinase inhibitors are gefitinib and erlotinib.

In some embodiments, the method of treating cancer further includes administering to a patient an antibody. In some embodiments, the method of treating cancer further includes administering to a patient an anti-HER-2 antibody, anti-EGFR antibody, or anti-VEGF antibody. In some embodiments, the antibody is trastuzumab. As used herein, the term "antibody" includes polyclonal, monoclonal, chimeric, humanized, and recombinant antibodies. As used herein, the term "anti-HER-2 antibody" refers to an antibody that inhibits the activity of HER-2. As used herein, the term "anti-VEGF antibody" refers to an antibody that inhibits the activity of vascular endothelial growth factor (VEGF). As used herein, the term "anti-EGFR antibody" refers to an antibody that inhibits the activity of EGFR. Example anti-HER-2 antibodies include, but are not limited to, trastuzumab (Herceptin™), 2C4, 4D5, HER-50, HER-66, HER-70 (available from Genentech or UT Southwestern Medical School) and the like. Example anti-EGFR antibodies include, but are not limited to, IMC-C225 (Imclone), ABX-EGF (Abgenix), and the like.

In some embodiments, the method of treating cancer further includes administering to a patient a chemotherapeutic agent. As used herein, the term "chemotherapeutic agent" refers any compound or substance that can be used to treat cancer.

Suitable chemotherapeutic agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic agents also include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), mithramycin, deoxyco-formycin, mitomycin-C, L-asparaginase, interferons (especially IFN-a), etoposide, and teniposide.

Other suitable chemotherapeutic agents include cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; leucovorin; tegafur; and haematopoietic growth factors.

Microtubule affecting agents interfere with cellular mitosis and are well known in the art for their cytotoxic activity. Microtubule affecting agents suitable as chemotherapeutic agents include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol™, NSC 125973), Taxol™ derivatives (e.g., derivatives NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, epothilone B, and discodermolide (see Service, 1996, Science 274:2009) estramustine, nocodazole, MAP4, and the like. Examples of such agents are also described in the scientific and patent literature, see, e.g., Bulinski, 1997, J. Cell Sci. 110:3055-3064; Panda, 1997, Proc. Natl. Acad. Sci. USA 94:10560-10564; Muhlradt, 1997, Cancer Res. 57:3344-3346; Nicolaou, 1997, Nature 387:268-272; Vasquez, 1997, Mol. Biol. Cell. 8:973-985; Panda, 1996, J. Biol. Chem 271: 29807-29812.

The term "paclitaxel" as used herein refers to the drug commercially available as Taxol™ (NSC number: 125973). Taxol™ inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz, 1992, Trends Pharmacol. Sci. 13: 134-146, Rowinsky, 1990, J. Natl. Canc. Inst. 82:1247-1259).

Further example chemotherapeutic agents are compounds with paclitaxel-like activity. These include, but are not limited to, paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

Further example chemotherapeutic agents are docetaxel (also known as Taxotere™), 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel (disclosed in U.S. Pat. No. 6,537,988), C-4 methyl carbonate paclitaxel (disclosed in WO 94/14787), epothilone A, epothilone B, epothilone C, epothilone D, desoxyepothilone A, desoxyepothilone B, [1S-[1R*,3R*(E),7R*,10S*,11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione (disclosed in U.S. Pat. Nos. 6,262,094 and 6,537,988), and derivatives thereof; and microtubule-disruptor agents.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference in its entirety.

The present invention further provides methods of inducing tumor cell death, programmed (e.g. apoptosis) or otherwise, in a patient comprising treating the patient in need thereof with hormone therapy and administering to the patient a therapeutically effective amount of at least one metalloprotease inhibitor (MPI).

The present invention additionally provides a method of inhibiting growth of a tumor in a patient by treating a patient with hormone therapy and administering to the patient a therapeutically effective amount of at least one MPI.

The present invention also provides a method of lowering a patient's resistance to hormone therapy by treating a patient with hormone therapy and administering to the patient a therapeutically effective amount of at least one MPI.

The present invention also provides a method of inhibiting onset of a hormone refractory state by treating a patient with hormone therapy and administering to the patient a therapeutically effective amount of at least one MPI.

The present invention also provides a method of inhibiting tumor cell proliferation by treating a patient with hormone therapy and administering to the patient a therapeutically effective amount of at least one MPI.

The present invention also provides a method of inhibiting metastasis of cancer by treating a patient with hormone therapy and administering to the patient a therapeutically effective amount of at least one MPI.

The present invention also provides a method of inducing quiescence in tumor cell growth after the cessation of treatment by treating a patient with hormone therapy and administering to the patient a therapeutically effective amount of at least one MPI for a period of time, followed by ceasing of treatment with one or both of the hormone therapy and MPI. The period of time of treatment can by any length of time sufficient to have a therapeutic effect.

Non-limiting examples of cancers treatable by the methods herein include acute myeloid lymphoma, adrenal carcinoma, bone cancer, brain cancer, brain cancer, breast cancer, bronchial cancer, cervical cancer, choriocarcinoma, chronic lymphocytic leukemia, chronic myelogenous leukemia, colon cancer, colorectal cancer, endometrial cancer, esophagial cancer, eye cancer, fallopian tube cancer, gastrointestinal cancer, glioma, hairy cell leukemia, hepatoma, Hodgkin's disease, intrahepatic bile duct cancer, joint cancer, Kaposi's sarcoma, kidney cancer, larynx cancer, liver cancer, lung cancer, lymphoblastic leukemia, lymphoma, malignant mesothelioma, medullobastoma, middle ear cancer, multiple myeloma, myeloma, nasal cavity cancer, nasopharynx cancer, neuroblastoma, Non-Hodgkin's lymphoma, non-small cell lung cancer, nose cancer, oral cavity cancer, ovarian cancer, pancreatic cancer, peritoneum cancer, pituitary gland cancer, prostate cancer, renal cancer, skin cancer, soft tissue sarcoma, stomach cancer, thyroid cancer, urinary cancer, uterine cancer, vaginal cancer, vesticular cancer, and Wilm's tumor. In some embodiments, the cancer to be treated is breast cancer, prostate cancer, uterine cancer, ovarian cancer, colon cancer, endometrial cancer, adrenal carcinoma, or non-small cell lung cancer. In some embodiments, the cancer is breast cancer or prostate cancer. In some embodiments, the cancer is prostate cancer. In some embodiments, the cancer is breast cancer.

As used herein, the term "patient" refers to any animal, including mammals, preferably mice, rats, other rodents, rabbits, dogs, cats, swine, cattle, sheep, horses, primates, or humans in need of treatment for cancer or similar disease. In some embodiments, the patient is human. In some embodiments, the patient is female and said cancer is breast cancer.

In the methods herein, said hormone therapy can be surgical treatment, such as oophorectomy, orchiectomy, adrenalectomy, or hypophysectomy, radiation treatment, where the organs or glands of said patient are exposed to a therapeutically effective amount of radiation, or administration of a therapeutically effective amount of at least one hormone therapy agent. When said hormone therapy comprises surgical treatment, the MPI of the methods herein may be administered to the simultaneously or substantially simultaneously with the subjection of the patient to the surgical method. The MPI may also be administered before or after the patient is subjected to the surgical method.

When the hormone therapy comprises radiation treatment, the MPI may be administered simultaneously, substantially simultaneously, or sequentially with the radiation treatment.

When the hormone therapy comprises the administration of at least one hormone therapy agent, said hormone therapy agent can be administered simultaneously with the MPI in a single dosage form (such as the pharmaceutical compositions of the present invention), or the hormone therapy agent and the MPI can be administered simultaneously, substantially simultaneously, or sequentially as separate dosage forms.

In some embodiments, the method of treating cancer further includes administering to an additional therapeutic agent. As used herein, the term "additional therapeutic agent" refers to an EGFR tyrosine kinase inhibitor, antibody, anti-HER-2 antibody, anti-EGFR antibody, anti-VEGF antibody, or a chemotherapeutic agent that is administered in addition to the hormone therapy and MPI. When the hormone therapy comprises a surgical treatment, the additional therapeutic agent may be administered to the patient in need thereof simultaneously or substantially simultaneously with the subjection of said patient to the surgical treatment. The additional therapeutic agent may also be administered before or after the patient is subjected to the surgical treatment. When the hormone therapy comprises administration of radiation, the additional therapeutic agent, radiation, and MPI may be administered simultaneously, substantially simultaneously, or sequentially. When the hormone therapy comprises the administration of at least one hormone therapy agent, the hormone therapy agent, MPI, and additional therapeutic agent can be administered simultaneously in a single dosage form, or the hormone therapy agent, the MPI, and the additional therapeutic agent can be administered simultaneously, substantially simultaneously, or sequentially as separate dosage forms.

In any method of treatment that further comprises an additional therapeutic agent, the additional therapeutic agent and MPI may be administered simultaneously in a single dosage form (such as the pharmaceutical compositions of the present invention) or can be administered simultaneously, substantially simultaneously, or sequentially as separate dosage forms.

All of the methods described herein also include regimens where treatment with the MPI, hormone therapy, or additional therapeutic agent is interrupted for a set period of time and then resumed. These interruptions can occur once or several times during the span of treatment.

As used herein, the phrase "therapeutically effective amount" refers to the amount of active compound (e.g., the MPI, hormone therapy agent) or the power or intensity of radiation that elicits the biological or medicinal response in a tissue, system, animal, individual or human that is being sought by a researcher, veterinarian, medical doctor or other clinician, which includes one or more of the following:

(1) preventing the cancer disease; for example, preventing a cancer in an individual that may be predisposed to cancer, but does not yet experience or display the pathology or symptomotology of the disease;

(2) inhibiting the cancer disease; for example, inhibiting cancer in an individual that is experiencing or displaying the pathology or symptomotology of the disease (i.e., arresting further development of the pathology and/or symptomotology); and (3) ameliorating the cancer disease; for example, ameliorating a disease, condition or disorder in an individual that is experiencing or displaying the pathology or symptomotology of the disease (i.e., reversing the pathology and/or symptomotology).

The precise therapeutically effective amount for a patient will depend upon the patient's size and health, the nature and extent of the condition, and the therapeutics or combination of therapeutics selected for administration. However, the effective amount for a given situation is determined by routine experimentation and is within the judgment of the clinician.

The active ingredients described herein can be administered by a variety of routes including oral, rectal, transdermal, subcutaneous, intravenous (including bolbus or infusion), intramuscular, intraperitoneal, and intranasal forms, and can be prepared in a manner well known in the pharmaceutical art. As used herein, the term "active ingredient(s)" refers to the MPI, hormone therapy agent, or additional therapeutic agent, or combinations thereof. Oral administration routes include, but are not limited to, tablets, capsules (each of which includes sustained release or timed release formulations), pills, powders, granules, elixirs, tinctures, suspensions, syrups, and emulsions. The active ingredients (MPIs, hormone therapy agents and/or additional therapeutic agents) can be administered alone but generally will be administered with a pharmaceutically acceptable carrier selected on the basis of the chosen route of administration and standard pharmaceutical practice.

Generally, the daily dosage of each active ingredient, when used for the indicated effects, will range between about 0.0001 to 1000 mg/kg of body weight per day. In some embodiments, the daily dosage of each individual active ingredient will be between about 0.01 to about 100 mg/kg of body weight per day. In some embodiments, the daily dosage of each individual active ingredient will be between about 0.1 to about 100 mg per/kg of body weight per day. In some embodiments, the intravenous daily dosage for each active ingredient will range from about 0.1 to about 10 mg/kg/minute during a constant rate infusion.

In some embodiments, the active ingredients are administered in an oral dosage form containing about 1 to about 1000 milligrams of each active ingredient, or more particularly, about 1, about 10, about 50, about 100, about 200, about 500, and about 1000 milligrams of each active ingredient for the symptomatic adjustment of the dosage to the patient to be treated. The active ingredients may be administered on a regimen of 1 to 4 times per day, preferably once or twice per day.

The active ingredients can also be administered in intranasal form via topical use of suitable intranasal vehicles, or via transdermal routes, using transdermal skin patches. When administered in the form of a transdermal delivery system, the dosage administration of that particular ingredient will, of course, be continuous rather than intermittent throughout the dosage regimen.

The proportion or concentration of the active ingredient in a pharmaceutical composition can vary depending upon a number of factors including dosage, chemical characteristics (e.g., hydrophobicity), and the route of administration. For example, the compounds of the invention can be provided in an aqueous physiological buffer solution containing 0.1 to 10% w/v of the compound for parenteral administration. Some typical dose ranges are from 1 μg/kg to 1 g/kg of body weight per day. In some embodiments, the dose range is from 0.01 mg/kg to 100 mg/kg of body weight per day. The dosage is likely to depend on such variables as the type and extent of progression of the disease or disorder, the overall health status of the particular patient, the relative biological efficacy of the compound selected, formulation of the excipient, and the route of administration. Effective doses can be extrapolated from dose-response curves derived from in vitro or animal model test systems.

When an active ingredient is formulated as a pharmaceutical composition, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. The active ingredients can also be formulated so as to provide quick, sustained or delayed release of the active ingredient after administration to the patient by employing procedures known in the art.

In preparing a formulation, the active ingredient(s) can be milled to provide the appropriate particle size prior to combining with the pharmaceutically acceptable carrier and other excipients. If the active ingredient is substantially insoluble, it can be milled to a particle size of less than about 200 mesh. If the active ingredient is substantially water soluble, the particle size can be adjusted by milling to provide a substantially uniform distribution in the formulation, e.g. about 40 mesh.

The active ingredient(s) can also be provided to a patient in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

The active ingredient(s) may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or poly-ethyleneoxide-polylysine substituted with palmitoyl residues. Furthermore, the active ingredient(s) may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, and crosslinked or amphipathic block copolymers of hydrogels.

Pharmaceutical compositions, such as those of the present invention and those used in the methods of the present invention, can be formulated in a unit dosage form, each dosage containing from about 0.0001 to about 1000 mg of each active ingredient. In some embodiments, each dosage contains about 0.01 to about 100 mg of each active ingredient. In some embodiments, each dosage contains about 0.1 to about 100 mg of each active ingredient. The term "unit dosage forms" refers to physically discrete units suitable as unitary dosages for human subjects and other mammals, each unit containing a predetermined quantity of the active ingredient calculated to produce the desired therapeutic effect, in association with a suitable pharmaceutical excipient.

The active ingredients can be effective over a wide dosage range and are generally administered in therapeutically effective amounts. It will be understood, however, that the amount of the active ingredient actually administered will usually be determined by a physician, according to the relevant circumstances, including the condition to be treated, the chosen route of administration, the actual compound administered, the age, weight, and response of the individual patient, the severity of the patient's symptoms, and the like.

Pharmaceutical compositions containing the active ingredient(s) can be in the form of tablets, pills, or capsules. For preparing solid compositions such as tablets, the principal active ingredient is mixed with a pharmaceutical excipient to form a solid preformulation composition containing a homogeneous mixture of the active ingredient. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.0001 to about 1000 mg of the active ingredients of the present invention.

Tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Gelatin capsules can also be used as dosage forms and may contain the active ingredient(s) and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Pharmaceutical compositions of the active ingredients for oral or injection administration can be prepared as well. The liquid forms in which the active ingredients of the present invention can be incorporated include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Pharmaceutical compositions for parenteral administration generally contain a water soluble salt of the active ingredient, suitable stabilizing agents, and if necessary, buffer substances. Generally, water, a suitable oil, saline, aqueous dextrose (glucose), and related sugar solutions and glycols such as propylene glycol or polyethylene glycols are suitable carriers for parenteral solutions. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in the field of pharmacology, incorporated herein by reference in its entirety.

Pharmaceutical compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The pharmaceutical compositions may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

The pharmaceutical compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

For topical use, creams, ointments, jellies, solutions or suspensions, containing the active ingredient(s) are employed. As used herein, topical application is also meant to include the use of mouth washes and gargles.

Representative useful pharmaceutical dosage-forms for administration of the active ingredients can be illustrated as follows:

Capsules

A large number of unit capsules can be prepared by filling standard two-piece hard gelatin capsules each with 50 milligrams of each active ingredient, powdered, 100 milligrams of lactose, 25 milligrams of cellulose, and 3 milligrams magnesium stearate.

Soft Gelatin Capsules

A mixture of active ingredients in a digestible oil such as soybean oil, cottonseed oil or olive oil may be prepared and injected by means of a positive displacement pump into gelatin to form soft gelatin capsules containing 75 milligrams of each active ingredient. The capsules can be washed and dried.

Tablets

Tablets may be prepared by conventional procedures so that the dosage unit is 75 milligrams of each active ingredient, 0.15 milligrams of colloidal silicon dioxide, 4 milligrams of magnesium stearate, 250 milligrams of microcrystalline cellulose, 9 milligrams of starch and 75 milligrams of lactose. Appropriate coatings well known to one skilled in the art may be applied to increase palatability and/or delay absorption.

Injectable

A parenteral composition suitable for administration by injection may be prepared by stirring 1.0% by weight of each active ingredient in 8% by volume propylene glycol and water. The solution should be made isotonic with sodium chloride and sterilized.

Suspension

An aqueous suspension can be prepared for oral administration so that each 5 mL contains 75 mg of finely divided preparation of each active ingredient, 150 mg of sodium carboxymethyl cellulose, 3.75 mg of sodium benzoate, 0.75 g of sorbitol solution, U.S.P., and 0.015 mL of vanillin.

The present invention also provides a pharmaceutical composition comprising at least one metalloprotease inhibitor (MPI), at least one hormone therapy agent, and a pharmaceutically acceptable carrier.

In some embodiments, the pharmaceutical composition further comprises at least one EGFR tyrosine kinase inhibitor.

In some embodiments, the pharmaceutical composition further comprises at least one antibody. In some embodiments, the pharmaceutical composition further comprises at least one anti-HER-2 antibody, anti-EGFR antibody, or anti-VEGF antibody. In some embodiments, the pharmaceutical composition further comprises trastuzumab.

In some embodiments, the pharmaceutical composition further comprises at least one chemotherapeutic agent.

In order that the invention disclosed herein may be more efficiently understood, examples are provided below. It should be understood that these examples are for illustrative purposes only and are not to be construed as limiting the invention in any manner.

EXAMPLES

Example 1

Effect of methyl (6S,7S)-7-[(hydroxyamino)carbonyl]-6-[(4-phenylpiperazin-1-yl)carbonyl]-5-azaspiro[2.5]octane-5-carboxylate (Compound 1), Alone and in Combination with the Hormone Therapy Agent, Fulvestrant, on the Growth of MCF-7 Breast Cancer Xenograft Preparation and Implantation of MCF-7 Xenograft into Test Animals:

Human breast cancer cell line MCF-7 was obtained from American Type Tissue Culture Collection (ATCC, Manassas, Va.). Cells were routinely maintained in media recommended by the ATCC with slight modifications. Cells were kept at 37° C. in a humidified incubator supplied with 5% $CO_2$. MCF-7 cells were kept in Eagle's minimal essential medium (ATCC) supplemented with 10% FBS and 0.01 mg/ml bovine insulin.

Animal studies were performed under Animal Welfare Regulation Guidelines in a facility accredited by the Association for the Assessment and Accreditation of Laboratory Animal Care (AAALAC). Balb/c or CD-1 nu/nu mice (Charles River, Wilmington, Mass.) were injected subcutaneously with logarithmically growing cells suspended in either serum free culture media, or a 1:1 mixture media and Matrigel™ (BD Biosciences). The tumor models required implantation (on the same day or one day prior to cell inoculation) of estradiol pellets (17-β estradiol, 0.72 mg/pellet, 60 day release; Innovative Research of American, Sarasota, Fla.). The time in days after injection of the tumor cells into the mice was measured as "days post-inoculation".

Drug Delivery Mechanisms:

Subcutaneous implantation of osmotic pumps (obtained from Alzet, Cupertino, Calif.) was performed under isofluorane anesthesia following manufacturer's protocol. Subcutaneous pumps (hereinafter "SC pumps") were used to deliver a solution of Compound 1, or its inert solvent. Fulvestrant, or its inert solvent, was delivered by subcutaneous injection on the dorsal flanks of the animals. Treatment was usually initiated when mean tumor volumes were approximately 150 mm³ at the beginning of treatment. Ten test animals were included in each treatment group, (a)-(d).

Tumor Size Measurements and Mean Tumor Volume Calculation:

Tumor size was measured and used to calculate tumor volume for a period of time following the injection of the tumor cells into the mice. Tumor size was measured by using a caliper to measure the length (l) and width (w) of tumors to calculate an approximate volume ((l×w²)/2). These tumor size measurements and tumor volume calculations were recorded relative to the number of days post-inoculation of the mice with the tumor cells. The frequency of the tumor size measurements varied depending on how quickly the tumors grew in size, with more frequent measurements being taken when the tumors grew quickly. Mean tumor volume was calculated based on the tumor volumes for the ten test animals in each treatment group.

Treatment Regimens and Data Collection:

Treatment group (a) was the control group of test animals. Ten inoculated mice were treated continuously for 14 days with inert solvent in a volume equivalent to that used to deliver methyl (6S,7S)-7-[(hydroxyamino)carbonyl]-6-[(4-phenylpiperazin-1-yl)carbonyl]-5-azaspiro[2.5]octane-5-carboxylate (Compound 1; see U.S. Patent App. Pub. No. 2004/0259896, which is incorporated herein by reference in its entirety, for preparation and characterization of this compound) for treatment groups (b) and (d). The inert solvent was delivered by SC pump. The beginning and end of the 14 day treatment period are indicated by a horizontal arrow below the x-axis of FIG. 1. Additionally, the test animals were treated once per week for four weeks with castor oil in a volume equivalent to that used to deliver fulvestrant for treatment groups (c) and (d). The four weekly treatments of castor oil are separately indicated by the four vertical arrows above the x-axis of FIG. 1. Tumor size was measured for each test animal as described above and recorded as a function of the number of days post-inoculation of the mice with the MCF-7 breast cancer cells. Mean tumor volume was then calculated for treatment group (a) and plotted against the number of days post-inoculation as shown in FIG. 1.

The test animals in treatment group (b) were treated with Compound 1 alone. Ten inoculated mice were treated once per day for 14 days with 60 mg/kg/day of a solution of Compound 1 in inert solvent. The mg/kg/day doses were based on a weight of a 20 g mouse, which is the average weight of a mouse. The beginning and end of the 14 day treatment period are indicated by a horizontal arrow below the x-axis of FIG. 1. Additionally, the test animals were treated once per week for four weeks with castor oil in a volume equivalent to that used to deliver fulvestrant for treatment groups (c) and (d). The four weekly treatments of castor oil are separately indicated by the four vertical arrows above the x-axis of FIG. 1. Tumor size was measured for each test animal as described above and recorded as a function of the number of days post-inoculation of the mice with the MCF-7 breast cancer cells. Mean tumor volume was then calculated for treatment group (b) and plotted against the number of days post-inoculation as shown in FIG. 1.

The test animals in treatment group (c) were treated with fulvestrant alone. Ten inoculated mice were treated once per day for 14 days with inert solvent in a volume equivalent to that used to deliver Compound 1 for treatment groups (b) and (d). The beginning and end of the 14 day treatment period are indicated by a horizontal arrows below the x-axis of FIG. 1. Additionally, the test animals were treated once per week for four weeks with a solution of 5 mg of fulvestrant in castor oil. The four weekly treatments of fulvestrant are separately indicated by the four vertical arrows above the x-axis of FIG. 1. Tumor size was measured for each test animal as described above and recorded as a function of the number of days post-inoculation of the mice with the MCF-7 breast cancer cells. Mean tumor volume was then calculated for treatment group (c) and plotted against the number of days post-inoculation as shown in FIG. 1.

The test animals in treatment group (d) were treated with Compound 1 and fulvestrant in combination. Ten inoculated mice were treated once per day for 14 days with 60 mg/kg/day of a solution of Compound 1 in inert solvent. The mg/kg/day doses were based on a weight of a 20 g mouse, which is the average weight of a mouse. The beginning and end of the 14 day treatment period are indicated by a horizontal arrow below the x-axis of FIG. 1. Additionally, the test animals were treated once per week for four weeks with a solution of 5 mg of fulvestrant in castor oil. The four weekly treatments of fulvestrant are separately indicated by the four vertical arrows above the x-axis of FIG. 1. Tumor size was measured for each test animal as described above and recorded as a function of the number of days post-inoculation of the mice with the MCF-7 breast cancer cells. Mean tumor volume was then calculated for treatment group (d) and plotted against the number of days post-inoculation as shown in FIG. 1.

Summary of the Results:

The MCF-7 tumor model grows in athymic mice in an estrogen-dependent manner and is sensitive to perturbations in EGFR signaling despite not having an amplified HER-2 mutation. Treatment with the Compound 1, as in treatment group (b), inhibited tumor cell growth by 46% over the control group (a) (see FIG. 1). Treatment with the estrogen receptor downregulator (fulvestrant), as in treatment group (c), inhibited tumor cell growth by 52% (see FIG. 1). The combination of fluvestrant and Compound 1, as in treatment group (d), however, dramatically inhibited tumor growth by 78% (see FIG. 1). Additionally, the effects of the combination therapy were long lasting as the tumors treated with the combination regimen were static 75 days after the cessation of treatment. Linear regression analysis of each treatment group's tumor growth rate was used to calculate the projected time it would take each group to reach a predetermined size, 1000 cubic mm in this case. This permits one to quantify the long term effects of treatment by subtracting the control group from each treated group (T-C). When tumor growth delay (TGD) was calculated based on linear regression analysis of each treatment group's tumor growth curves to 1000 cubic mm, Compound 1 provided a 32 day TGD (real, not calculated) and fluvestrant a calculated 63 day TGD. The combination of these two agents, however, provided a calculated 226 day TGD. These results show that the combination of hormone therapy with a MPI can have a synergistic inhibitory effect on the growth of breast cancer tumor cells that grow in an estrogen dependent manner.

Example 2

Effect of Compound 1, Alone and in Combination with the Hormone Therapy Agent, Fulvestrant, on the Growth of BT-474 Breast Cancer Xenograft Preparation and Implantation of BT-474 Xenograft into Test Animals:

Human breast cancer cell line BT-474 was obtained from American Type Tissue Culture Collection (ATCC, Manassas, Va.). Cells were routinely maintained in media recommended by the ATCC with slight modifications. Cells were kept at 37°

C. in a humidified incubator supplied with 5% $CO_2$. BT-474 cells were grown in RPMI 1640 (Invitrogen) supplemented with 10% fetal bovine serum (FBS), 0.01 mg/ml bovine insulin, 10 mM HEPES and 0.1 mM non-essential amino acids.

Animal studies were performed under Animal Welfare Regulation Guidelines in a facility accredited by the Association for the Assessment and Accreditation of Laboratory Animal Care (AAALAC). Balb/c or CD-1 nu/nu mice (Charles River, Wilmington, Mass.) were injected subcutaneously with logarithmically growing cells suspended in either serum free culture media, or a 1:1 mixture media and Matrigel™ (BD Biosciences). The tumor models required implantation (on the same day or one day prior to cell inoculation) of estradiol pellets (17-βestradiol, 0.72 mg/pellet, 60 day release; Innovative Research of American, Sarasota, Fla.). The time in days after injection of the tumor cells into the mice was measured as "days post-inoculation".

Drug Delivery Mechanisms:

Subcutaneous implantation of osmotic pumps (obtained from Alzet, Cupertino, Calif.) was performed under isofluorane anesthesia following manufacturer's protocol. Subcutaneous pumps were used to deliver a solution of Compound 1, or its inert solvent. Fulvestrant, or its inert solvent, was delivered by subcutaneous injection on the dorsal flanks of the animals. Separate SC pumps were used to deliver the solutions of Compound 1 and fulvestrant and were implanted on the same day. Treatment was usually initiated when mean tumor volumes were approximately 150 $mm^3$ at the beginning of treatment. Ten test animals were included in each Treatment group, (a)-(d).

Tumor Size Measurements and Mean Tumor Volume Calculation:

Tumor size was measured and used to calculate tumor volume for a period of time following the injection of the tumor cells into the mice. Tumor size was measured by using a caliper to measure the length (l) and width (w) of tumors to calculate an approximate volume $((l \times w^2)/2)$. These tumor size measurements and tumor volume calculations were recorded relative to the number of days post-inoculation of the mice with the tumor cells. The frequency of the tumor size measurements varied depending on how quickly the tumors grew in size, with more frequent measurements being taken when the tumors grew quickly. Mean tumor volume was calculated based on the tumor volumes for the ten test animals in each treatment group.

Figure 2:
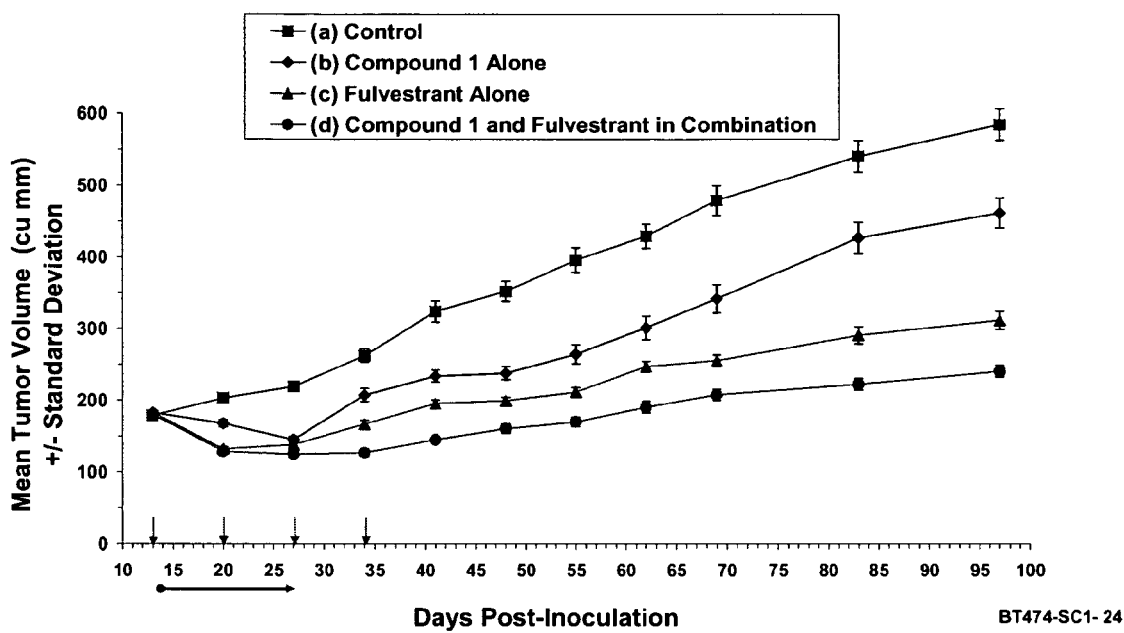
FIG. 2: Graph of mean tumor volume (cubic mm) for mice bearing subcutaneous BT-474 human breast cancer xenografts plotted as a function of the number of days post-inoculation of the tumors into the mice. These breast cancer cells have an amplified HER-2 mutation and grow in an estrogen dependent manner.

Treatment Regimens and Data Collection:

Treatment group (a) was the control group of test animals. Ten inoculated mice were treated once per day for 14 days with inert solvent in a volume equivalent to that used to deliver Compound 1 for treatment groups (b) and (d). The inert solvent was delivered by SC pump. The beginning and end of the 14 day treatment period are indicated by a horizontal arrow below the x-axis of FIG. 2. Additionally, the test animals were treated once per week for four weeks with castor oil in a volume equivalent to that used to deliver fulvestrant for treatment groups (c) and (d). The four weekly treatments of castor oil are separately indicated by the four vertical arrows above the x-axis of FIG. 2. Tumor size was measured for each test animal as described above and recorded as a function of the number of days post-inoculation of the mice with the BT-474 breast cancer cells. Mean tumor volume was then calculated for treatment group (a) and plotted against the number of days post-inoculation as shown in FIG. 2.

The test animals in treatment group (b) were treated with Compound 1 alone. Ten inoculated mice were treated once per day for 14 days with 60 mg/kg/day of a solution of Compound 1 in inert solvent. The mg/kg/day doses are based on a weight of a 20 g mouse, which is the average weight of a mouse. The beginning and end of the 14 day treatment period is indicated by a horizontal arrow below the x-axis of FIG. 2. Additionally, the test animals were treated once per week for four weeks with castor oil in a volume equivalent to that used to deliver fulvestrant for treatment groups (c) and (d). The four weekly treatments of castor oil are separately indicated by the four vertical arrows above the x-axis of FIG. 2. Tumor size was measured for each test animal as described above and recorded as a function of the number of days post-inoculation of the mice with the BT-474 breast cancer cells. Mean tumor volume was then calculated for treatment group (b) and plotted against the number of days post-inoculation as shown in FIG. 2.

The test animals in treatment group (c) were treated with fulvestrant alone. Ten inoculated mice were treated once per day for 14 days with inert solvent in a volume equivalent to that used to deliver Compound 1 for treatment groups (b) and (d). The beginning and end of the 14 day treatment period are indicated by a horizontal arrow below the x-axis of FIG. 2. Additionally, the test animals were treated once per week for four weeks with a solution of 5 mg of fulvestrant in castor oil. The four weekly treatments of fulvestrant are separately indicated by the four vertical arrows above the x-axis of FIG. 2. Tumor size was measured for each test animal as described above and recorded as a function of the number of days post-inoculation of the mice with the BT-474 breast cancer cells. Mean tumor volume was then calculated for treatment group (c) and plotted against the number of days post-inoculation as shown in FIG. 2.

The test animals in treatment group (d) were treated with Compound 1 and fulvestrant in combination. Ten inoculated mice were treated once per day for 14 days with 60 mg/kg/day of a solution of Compound 1 in inert solvent. The mg/kg/day doses are based on a weight of a 20 g mouse, which is the average weight of a mouse. The beginning and end of the 14 day treatment period is indicated by a horizontal arrow below the x-axis of FIG. 2. Additionally, the test animals were treated once per week for four weeks with a solution of 5 mg of fulvestrant in castor oil. The four weekly treatments of fulvestrant are separately indicated by the four vertical arrows above the x-axis of FIG. 2. Tumor size was measured for each test animal as described above and recorded as a function of the number of days post-inoculation of the mice with the BT-474 breast cancer cells. Mean tumor volume was then calculated for treatment group (d) and plotted against the number of days post-inoculation as shown in FIG. 2.

Summary of the Results:

The BT-474 human breast xenograft is an estrogen-dependent tumor model, which has an amplified HER-2 and which also sheds HER-2 extracellular domain. Treatment with Compound 1, as in treatment group (b), inhibited tumor cell growth by 33% over the control group (a) (see FIG. 2). Treatment with the estrogen receptor downregulator (fulvestrant), as in treatment group (c), inhibited tumor cell growth by 46% (see FIG. 2). The combination of fluvestrant and Compound 1, as in treatment group (d), however, was superior to either agent alone and inhibited tumor growth by 57% (see FIG. 2). The difference is best represented graphically by the slope of the tumor growth during the combination treatment period. Linear regression analysis of each treatment group's tumor growth rate was used to calculate the projected time it would take each group to reach a predetermined size, 500 cubic mm in this case. This permits one to quantify the long term effects of treatment by subtracting the control group from each treated group (T-C). Using this analysis, Compound 1 provided a 19 day TGD, fluvestrant provided a 54 day TGD, and the combination resulted in a 90 day TGD. These results show that the combination of hormone therapy with a MPI can have a synergistic inhibitory effect on the growth of breast cancer tumor cells that have amplified HER-2 expression.

All patents, patent applications and publications cited in this application are hereby incorporated herein by reference in their entirety for all purposes to the same extent as if each individual patent, patent application or publication were so individually denoted.

While the many forms of the invention herein disclosed constitute presently preferred embodiments, many others are possible and further details of the preferred embodiments and other possible embodiments are not to be construed as limitations. It is understood that the terms used herein are merely descriptive rather than limiting and that various changes may be made without departing from the spirit or scope of the claimed invention.

What is claimed is:

1. A pharmaceutical composition comprising at least one metalloprotease inhibitor (MPI), at least one hormone therapy agent, and a pharmaceutically acceptable carrier, wherein said MPI comprises methyl (6S,7S)-7-[(hydroxyamino)carbonyl]-6-[(4-phenylpiperazin-1-yl)carbonyl]-5-azaspiro[2.5]octane-5-carboxylate, or a pharmaceutically acceptable salt thereof; and wherein, the hormone therapy agent is fulvestrant.

2. A method of treating breast cancer comprising treating a patient in need thereof with a therapeutically effective amount of a composition of claim 1.

3. A method of treating breast cancer comprising treating a patient in need thereof with at least one hormone therapy agent and at least one metalloprotease inhibitor (MPI), wherein said hormone therapy agent comprises fulvestrant, and said at least one MPI comprises methyl (6S,7S)-7-[(hydroxyamino)carbonyl]-6-[(4-phenylpiperazin-1-yl)carbonyl]-5-azaspiro[2.5]octane-5-carboxylate, or a pharmaceutically acceptable salt thereof.

* * * * *

UNITED STATES PATENT AND TRADEMARK OFFICE
CERTIFICATE OF CORRECTION

PATENT NO. : 8,324,194 B2
APPLICATION NO. : 11/602659
DATED : December 4, 2012
INVENTOR(S) : Jordan S. Fridman Page 1 of 1

It is certified that error appears in the above-identified patent and that said Letters Patent is hereby corrected as shown below:

On the Title page
Item 56 OTHER PUBLICATIONS, Line 30, delete "Membrance" and insert
--Membrane--.

On the Title page
Item 56 OTHER PUBLICATIONS, Line 50, delete "Anitproliferative" and insert
--Antiproliferative--.

Signed and Sealed this
Twelfth Day of March, 2013

Teresa Stanek Rea
*Acting Director of the United States Patent and Trademark Office*

UNITED STATES PATENT AND TRADEMARK OFFICE
CERTIFICATE OF CORRECTION

Page 1 of 1

PATENT NO. : 8,324,194 B2
APPLICATION NO. : 11/602659
DATED : December 4, 2012
INVENTOR(S) : Jordan S. Fridman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this
Twenty-first Day of October, 2014

Michelle K. Lee
*Deputy Director of the United States Patent and Trademark Office*